US 8,174,701 B2

(12) United States Patent
Masuda

(10) Patent No.: US 8,174,701 B2
(45) Date of Patent: May 8, 2012

(54) OPTICAL TOMOGRAPHIC IMAGING SYSTEM

(75) Inventor: Tadashi Masuda, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 686 days.

(21) Appl. No.: 12/239,782

(22) Filed: Sep. 28, 2008

(65) Prior Publication Data

US 2009/0086213 A1  Apr. 2, 2009

(30) Foreign Application Priority Data

Sep. 28, 2007  (JP) ................................. 2007-255786

(51) Int. Cl.
*G01B 11/02* (2006.01)
(52) U.S. Cl. ....................................................... 356/479
(58) Field of Classification Search .................. 356/479, 356/497; 385/25, 26
See application file for complete search history.

(56) References Cited

U.S. PATENT DOCUMENTS

| | | | | |
|---|---|---|---|---|
| 5,265,301 | A * | 11/1993 | Irwin | 15/104.33 |
| 5,321,501 | A * | 6/1994 | Swanson et al. | 356/479 |
| 6,158,076 | A * | 12/2000 | Rutkowski et al. | 15/104.33 |
| 7,120,349 | B2 * | 10/2006 | Elliott | 385/137 |
| 7,304,296 | B2 * | 12/2007 | Mills et al. | 250/239 |
| 7,382,949 | B2 * | 6/2008 | Bouma et al. | 385/25 |
| 7,539,362 | B2 * | 5/2009 | Teramura et al. | 385/12 |
| 7,667,190 | B2 * | 2/2010 | Mills et al. | 250/239 |
| 7,692,797 | B2 * | 4/2010 | Kawahara | 356/497 |
| 7,881,569 | B2 * | 2/2011 | Zhang et al. | 385/26 |
| 2006/0093276 | A1 * | 5/2006 | Bouma et al. | 385/72 |
| 2006/0215170 | A1 * | 9/2006 | Toida et al. | 356/479 |
| 2007/0076215 | A1 * | 4/2007 | Toida | 356/497 |
| 2007/0081166 | A1 * | 4/2007 | Brown et al. | 356/479 |
| 2007/0115477 | A1 * | 5/2007 | Teramura et al. | 356/479 |
| 2007/0229846 | A1 * | 10/2007 | Blalock | 356/503 |
| 2009/0251704 | A1 * | 10/2009 | Masuda | 356/477 |
| 2009/0262361 | A1 * | 10/2009 | Tanioka et al. | 356/479 |
| 2009/0296086 | A1 * | 12/2009 | Appel et al. | 356/326 |

FOREIGN PATENT DOCUMENTS

| | | |
|---|---|---|
| JP | 11-225942 A | 8/1999 |
| JP | 2006-215005 A | 8/2006 |
| JP | 2007-206049 A | 8/2007 |
| JP | 2007-242747 A | 9/2007 |

OTHER PUBLICATIONS

Notification of Reasons for Refusal, dated Mar. 13, 2012, issued in corresponding JP Application No. 2007-255786, 8 pages In English and Japanese.

* cited by examiner

*Primary Examiner* — Michael A Lyons
*Assistant Examiner* — Scott M Richey
(74) *Attorney, Agent, or Firm* — Sughrue Mion, PLLC

(57) ABSTRACT

The optical tomographic imaging system includes a main body for acquiring an optical tomographic image, an optical probe having a rotary optical fiber for guiding the measuring and returning light, a measuring unit, and a sheath rotatably holding the rotary optical fiber and the measuring unit, a rotary drive unit for rotatably coupling the rotary optical fiber to a stationary optical fiber connected with the main body, an extra length handling mechanism for winding the optical probe into a loop having at least a minimum diameter and an attaching unit removably attaching the optical probe. The extra length handling mechanism winds an extra length of the optical probe by a length depending upon a length up to the location to be examined. The system eliminates the need to change the optical probe depending upon the location to be examined and the need to adjust the optical path length of reference light.

15 Claims, 10 Drawing Sheets

OPTICAL TOMOGRAPHIC IMAGING SYSTEM

BACKGROUND OF THE INVENTION

The present invention relates to an optical tomographic imaging system for acquiring a tomographic image of an object under measurement and more specifically to an optical tomographic imaging system comprising an optical probe rotatably holding an optical fiber that guides measuring light to the object under measurement and guides returning light from the object under measurement to acquire an optical tomographic image of the object under measurement, whereby the extra length of the optical probe can be handled according to a length up to the object under measurement at a location to be examined in such a manner as to permit adjustment of the use length of the optical probe according to the length to the object under measurement.

Acquisition of a cross-sectional image of a sample under measurement such as biological tissue without cutting thereinto may be achieved using an optical tomographic imaging system known in the art employing optical coherence tomography (OCT) measuring.

The OCT measuring is a kind of optical interferometric measurement using optical interference that occurs only when the optical path lengths of the measuring light and the reference light, into which the light from the light source is divided, are matched to within the coherence length of the light from the light source.

An optical tomographic imaging system using the OCT measuring is disclosed, for example, in JP 2006-215005 A filed by one of the Applicants of the present application, comprising a light source; optical splitting means for splitting the light emitted from the light source into measuring light and reference light; a probe including a measuring unit for irradiating the object under measurement with the measuring light and detecting the reflected light, an optical fiber for transmitting the measuring light and the reflected light, and a transparent tube covering the optical fiber and the measuring unit; optical path length changing means for changing the optical path length of the reference light to a length that is a sum of the optical path lengths of the measuring light and the reflected light; combining means for combining the reference light having its optical path length changed and the reflected light; and interference light detecting means for detecting interference light produced from the combined reference light and reflected light to generate a tomographic image from the detected interference light. With the optical tomographic imaging system disclosed in JP 2006-215005 A, the measuring unit located close to the tip of the probe is introduced to a position to be measured and rotated by turning the optical fiber to acquire tomographic images at a plurality of points on the object under measurement at a location to be measured as the measuring unit rotates, thus reconstructing a two-dimensional sectional image.

The optical path length changing means disclosed in JP 2006-215005 A comprises a first optical path length changing means for changing the optical path length of the reference light according to the sum of the optical path lengths of the measuring light and the reflected light that varies as the measuring position in the object under measurement in a depthwise direction is changed and a second optical path length changing means for changing the optical path length of the reference light to correct a manufacturing error made in the length of the probe that is attached to the main body of the system. Thus, in cases where two or more probes are used by replacing one with another depending upon the length required, when variations arise in the optical path lengths of the measuring light and the reflected light due to variations attributable to manufacturing errors in the lengths of the individual probes, the optical tomographic imaging system disclosed in JP 2006-215005 is capable of adjusting the optical path length of the reference light according to such variations using the second optical path length changing means and thus capable of preventing variation in the measuring range that might otherwise be caused by variation in length among the probes used. In particular, the system disclosed in JP 2006-215005 A is capable of accurately matching the measureable region with a set measuring region by preventing variation in the measuring range caused by variation in length among the probes with the two optical path length changing means.

SUMMARY OF THE INVENTION

Since the optical tomographic imaging system disclosed in JP 2006-215005 has the second optical path length changing means in addition to the first optical path length changing means that is necessary to change the measuring position in the object under measurement in a depthwise direction, the system permits accurate measuring as it is capable of adjusting the optical path length of the reference light according to the variations, if any, in the measuring light and the reflected light when such variations are of a degree comparable to a degree of variations attributable, for example, to manufacturing errors in length of the probes. However, the second optical path length changing means is composed of expensive optical elements and optical devices and is therefore costly, which is a factor to increase the costs of the optical tomographic imaging system.

Since the probe of the optical tomographic imaging system is used typically by inserting it into the forceps, etc. of the endoscope introduced to a location to be examined and touching it to the object under measurement at the location to be examined, and since the required length of the endoscope greatly varies depending upon the location to be examined, the length of the probe used varies greatly. Accordingly, different lengths of the endoscopes each suitable for examining different locations, for example, esophagus, bronchus, lung, stomach, duodenum, and small and large intestines, respectively call for different lengths of probes such as, for example, an esophagus measuring probe, a bronchus measuring probe, a lung measuring probe, a stomach measuring probe, a duodenum measuring probe, a small intestine measuring probe, and a large intestine measuring probe. Thus, a proper probe is attached to the optical tomographic imaging system in place of another depending upon the location to be examined for optical tomographic imaging.

Since a conventional optical tomographic imaging system of a kind described above requires probes each greatly different in length for different locations to be examined, a problem is posed that probes of different kinds must be had available for examining different locations. Accordingly, manufacturers and sellers must be ready at all times to provide numerous probes of different kinds for different locations to be examined, which necessitates not only inventory control of numerous probes but also a number of man-hours for development, manufacturing drawings, and management of many component parts, increasing the overall costs of the system. On the other hand, the users, for example hospitals, must have probes of different kinds available for examining different locations, which necessitates management of numerous probes of many kinds.

Conventional optical tomographic imaging systems further posed a problem that greatly different probe lengths that must be used for different locations to be examined resulted in a great difference in optical path length of the reference light, which in turn required optical fibers having different lengths for different lengths of the probes to guide the reference light, in addition to the trouble that had to be taken to replace the optical fiber for guiding the reference light with another having a different length each time a different length of probe is used. In addition, only a skilled person or an expert in maintenance could carry out such a change in the system configuration, but an operator of the endoscope or the optical tomographic imaging system or a medical person handling the system could not easily carry out changes of that kind.

One may consider using the second optical path length changing means disclosed in JP 2006-215005 to cope with the variation in optical path length according to the change in the probe length. However, a great change in the optical path length of the reference light cannot be readily addressed with the second optical path length changing means, which is only capable of making adjustments in variation in the optical path length of the reference light when the variation is of a degree comparable to a degree of variations attributable, for example, to manufacturing errors in length among the individual probes. Even though the difference in probe length is of such an amount as to permit adjustment using the second optical path length changing means, the second optical path length changing means is expensive and increases the overall costs of the whole system as described above.

The Applicants of the present application tiled a Japanese Patent Application No. 2006-335568, disclosing an optical tomographic imaging system wherein part of the optical fiber for guiding the reference light is removably provided to permit replacing the optical fiber with another having a proper length to change the optical path length of the reference light according to the probe length required that varies depending upon the location to be examined.

According to the optical tomographic imaging system disclosed in that application, the lengths of the optical fiber that must be had available depending upon the probe of which the length varies depending upon the location to be examined may be short, and replacement may be done fairly easily as compared with the cases where the whole length of the optical fiber for guiding the reference light is changed. However, there still remained problems that different kinds of optical fibers having different lengths that must be had available were required for different kinds of probes having different lengths and that the optical fiber for guiding the reference light needed to be changed either way even though it may be a partial change, and that was a difficult process to perform for an unskilled operator.

An object of the present invention is to provide an optical tomographic imaging system that solves the above problems associated with the prior art and can acquire a high-resolution optical tomographic image with ease of operation and a high efficiency without increasing the costs of the system while eliminating the need to have different lengths of optical probes for optical tomographic imaging available for different locations to be examined, the need to change the optical probe depending upon the location to be examined, hence the need of optical probe replacement operation to change the optical probe depending upon the location to be examined, and, as a result, the need to adjust the optical path length of the reference light that would otherwise be required upon replacing the optical probe with another having a different length, hence the need to have available a plurality of optical fibers for guiding the reference light (the whole length or part thereof) to adjust the optical path length of the reference light, the need to change the optical fiber, and the need to have an expensive optical path length changing means for adjusting the optical path length of the reference light.

To solve the above problems, the present invention provides an optical tomographic imaging system comprising a main body of system for acquiring an optical tomographic image of an object under measuring; an optical probe having a given length and including a first optical fiber rotatably provided for guiding measuring light from the main body of system to the object under measurement and guiding returning light from the object under measurement to the main body of system, a measuring unit disposed at a tip of the first optical fiber for irradiating the object under measurement with the measuring light and acquiring returning light from the object under measurement, and a probe sheath covering the peripheries of the first optical fiber and the measuring unit so as to rotatably hold the first optical fiber and the measuring unit and having at least a region thereof formed of a transparent material transmitting the measuring light from the measuring unit and the returning light from the object under measurement; a second optical fiber stationarily provided and connected with the main body of system for guiding the measuring light to the first optical fiber and guiding the returning light guided by the first optical fiber to the main body of system; a rotary drive unit provided between the optical probe and the second optical fiber for rotatably connecting the measuring unit and the first optical fiber following the measuring unit in the optical probe to the second optical fiber to transmit the measuring light and the returning light; an extra length handling mechanism for winding the optical probe into a circular loop having at least a given minimum diameter on a side closer to the rotary drive unit and holding the probe so wound; and attaching and detaching means for attaching and detaching the optical probe at the rotary drive unit or between the rotary drive unit and the extra length handling mechanism, wherein the main body of system acquires the optical tomographic image of the object under measurement using the guided returning light, and wherein the extra length handling mechanism winds an extra length of the optical probe according to the object under measurement to set a length extending from the extra length handling mechanism to a tip of the optical probe.

Preferably, the extra length handling mechanism comprises a restricting guide for winding the optical probe into the circular loop having at least a given minimum diameter.

Preferably, the extra length handling mechanism comprises a storage unit for storing the optical probe wound into the circular loop having at least a given minimum.

Preferably, the extra length handling mechanism comprises a mechanism for winding an extra length of the optical probe into a circular loop having a diameter of 100 mm or more not affecting rotational variation of the first optical fiber in the probe sheath of the optical probe.

Preferably, the rotary drive unit is an optical rotary adapter or an optical rotary joint for rotatably connecting the first optical fiber of the optical probe to the second optical fiber spaced with a given distance between these optical fibers to transmit the measuring light and the returning light.

Preferably, the attaching and detaching means is provided in the rotary drive unit to attach and detach the first optical fiber of the optical probe to the second optical fiber.

Preferably, the attaching and detaching means is an optical connector coupling unit or an optical adapter connecting mechanism provided between the extra length handling mechanism and the rotary drive unit to removably attach the first optical fiber of the optical probe.

Preferably, the optical probe is inserted into an endoscope introduced to a location to be examined such that a tip portion where the measuring unit is positioned is placed into contact with the object under measurement at the location to be examined for measurement, the optical probe being wound into the extra length handling mechanism by a length depending upon an insertion length up to the location to be examined to which the endoscope is introduced to set a length of the first optical fiber extending beyond the extra length handling mechanism.

Preferably, the main body of system comprises a light source; a splitter for splitting light emitted from the light source into the measuring light and reference light; a combiner for combining the returning light detected by the measuring unit of the optical probe and guided through the first optical fiber, the rotary drive unit, and the second optical fiber with the reference light to produce an interference light; an interference light detector for detecting the interference light as an interference signal; and a tomographic image acquirer for acquiring the optical tomographic image from the interference signal detected by the interference light detector.

Preferably, the light source emits light as it sweeps a wavelength with a constant period.

Preferably, the rotary drive unit is an optical rotary adapter comprising a fixed sleeve, the second optical fiber supported by the fixed sleeve and having an end face on one end thereof that is inclined a given angle with respect to a plane perpendicular to the optical axis thereof, a second collimating lens, which is stationary, spaced a given distance from the inclined end face of the second optical fiber, a mounting cylinder supported rotatably with respect to the fixed sleeve, a first optical fiber fixedly mounted substantially at the center of the mounting cylinder, disposed opposite the second collimating lens, and having an end face inclined a given angle with respect to a plane perpendicular to the optical axis of the second collimating lens, a first collimating lens, which is rotary, fixedly mounted to substantially the center of the mounting cylinder and disposed between the second collimating lens and the first optical fiber with a given distance from the inclined end face of the first optical fiber, and rotary drive means for rotating the mounting cylinder, wherein the optical axes of the second optical fiber and the first optical fiber are disposed in an offset position with respect to the central axis of rotation of the mounting cylinder to reduce the attenuation of the returning light.

Preferably, offset amounts $\delta 1$ and $\delta 2$ of the respective optical axes of the second optical fiber and the first optical fiber with respect to the central axis of rotation of the mounting cylinder satisfy the following equations (1), (2), (3), and (4)

$$n1 \times \sin\theta 1 = n3 \times \sin\theta 3 \quad (1)$$

$$\delta 1 = f1 \times \tan(\theta 3 - \theta 1) \quad (2)$$

$$n2 \times \sin\theta 2 = n3 \times \sin\theta 4 \quad (3)$$

$$\delta 2 = f2 \times \tan(\theta 4 - \theta 2) \quad (4)$$

where $\theta 1$ and $\theta 2$ are the inclination angles of the inclined end faces of the second optical fiber and the first optical fiber with respect to planes perpendicular to the optical axes thereof, n1 and n2 are the refractive indexes of the second optical fiber and the first optical fiber, n3 is the refractive index of the medium between the second optical fiber and the first optical fiber through which light propagates, $\theta 3$ and $\theta 4$ are the angles of the light traveling through the second optical fiber and the first optical fiber in the direction parallel to the optical axes thereof and refracted at interfaces between the inclined end faces and the medium with respect to the normal lines to the inclined end faces, respectively, f1 and f2 are respectively the focal distances of the second collimating lens and the first collimating lens equal respectively to the distances along the optical axes between the centers of the inclined end faces of the second optical fiber and the first optical fiber and the centers of the second collimating lens and the first collimating lens, respectively, on the assumption that the second collimating lens and the first collimating lens are thin sheet lenses.

Preferably, the second optical fiber and the second collimating lens are disposed symmetrically to the first optical fiber and the first collimating lens.

Preferably, the second optical fiber and the first optical fiber are each supported by ferrules, which have inclined end faces lying in the same planes as the second optical fiber and the first optical fiber, respectively.

Preferably, the mounting cylinder fixedly supporting the first optical fiber and the first collimating lens is detachably attached to the fixed sleeve fixedly supporting the second optical fiber and the second collimating lens.

Preferably, the optical rotary adapter further comprises a rotary cylinder having one end thereof attached to the mounting cylinder so as to rotate about the central axis of rotation unitarily with the mounting cylinder, wherein the inclined end face of the first optical fiber on one end thereof is attached to the mounting cylinder such that the optical axis thereof is offset with respect to the central axis of rotation of the mounting cylinder and wherein the first optical fiber is supported by the rotary cylinder at the other end of the rotary cylinder.

At the other end of the rotary cylinder, the first optical fiber is preferably supported at the center of the rotary cylinder such that the optical axis of the first optical fiber coincides with the central axis of rotation of the mounting cylinder.

Preferably, the first optical fiber has another end face at the other end of the rotary cylinder forming a fixed type optical connector, and the other end face of the first optical fiber is attached to the center of the rotary cylinder such that the optical axis of the first optical fiber coincides with the central axis of rotation of the mounting cylinder.

Alternatively, it is preferable that the first optical fiber extends from the other end of the rotary cylinder and that its forward end is connected to the measuring unit that illuminates the object under measurement with the measuring light to acquire returning light therefrom and is rotatably held by a transparent probe sheath to form part of the optical probe.

Since the optical tomographic imaging system of the invention needs an optical probe of only one kind for different lengths of endoscopes used for examining different locations, there is no need to have available different lengths of optical probes for different locations to be examined, reducing the man-hours for development and manufacturing drawings as well as the burden of management of component parts while eliminating the need of inventory control of numerous optical probes of many kinds, thereby reducing the overall costs of the system as a whole.

Further, the present invention eliminates the need to perform the optical probe replacement operation for changing the optical probe depending upon the location to be examined and, as a result, the need of a function and an operation to adjust the optical path length of the reference light that would otherwise be required upon replacing the optical probe with another having a different length, hence the need to have a plurality of optical fibers for guiding the reference light (the whole length or part thereof) to adjust the optical path length of the reference light, and the need to change the optical fiber for guiding the reference light. Thus, the present invention provides an optical tomographic imaging system permitting ease of operation and a high operating efficiency. As a result, the present invention permits preventing deterioration of the end faces of the optical fibers that would otherwise occur from replacements of optical probes and optical fibers and hence lowering of performance and performance reliability.

Further, the present invention eliminates the need of an expensive optical path length changing means to provide a function of adjusting the optical path length of the reference light upon replacement of the optical probe, which keeps the overall costs of the system from increasing accordingly.

This produces an effect of providing an optical tomographic imaging system capable of acquiring a high resolution tomographic image of an object under measurement with ease of operation and a high operating efficiency.

BRIEF DESCRIPTION OF THE DRAWINGS

These and other objects, features, and advantages of the present invention will be apparent from the following detailed description and accompanying drawings in which.

DETAILED DESCRIPTION OF THE INVENTION

Now, the inventive optical tomographic imaging system will be described in detail referring to the preferred embodiments illustrated in the attached drawings.

Figure 1:
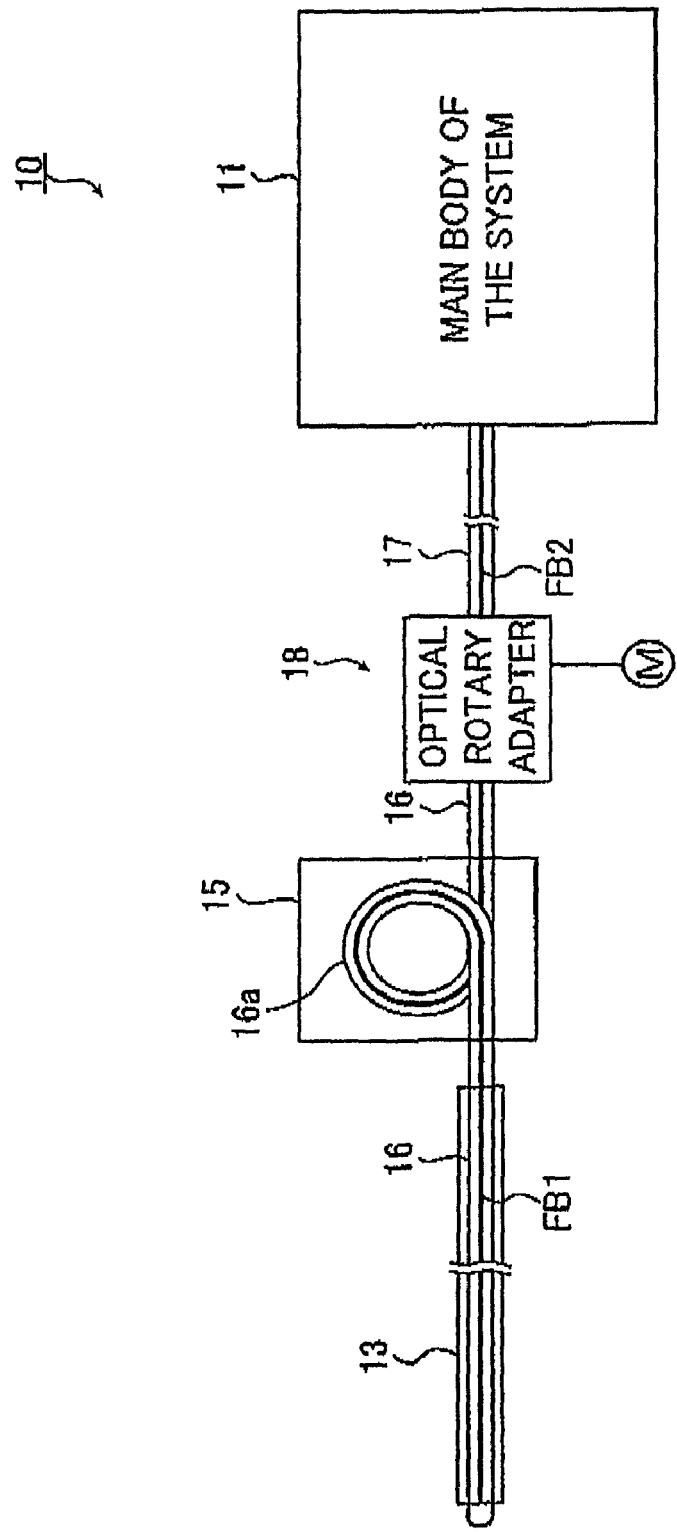
FIG. 1 is a view for explaining a schematic configuration of an embodiment of the optical tomographic imaging system of the invention.
Figure 2:
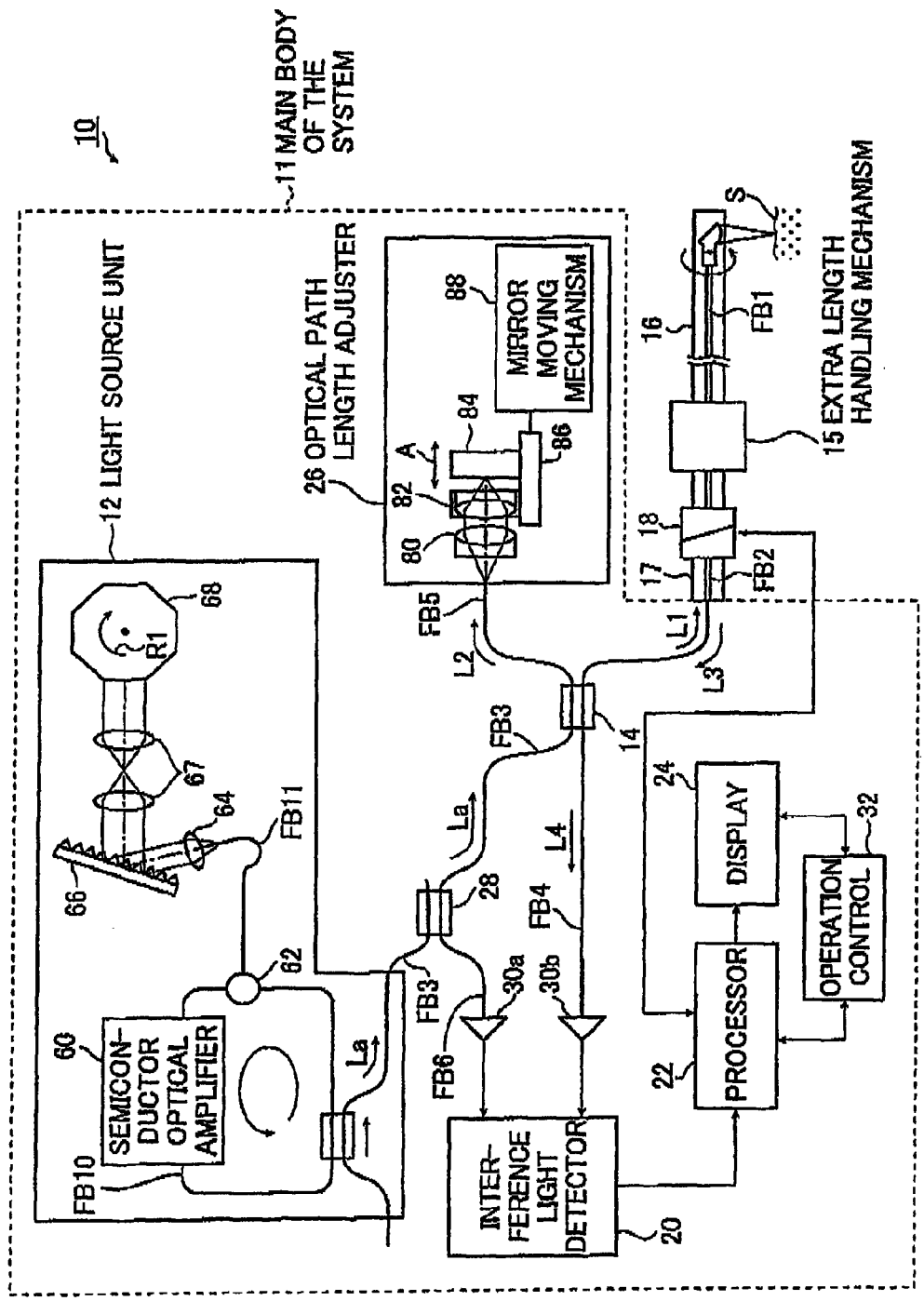
FIG. 2 is a block diagram illustrating a schematic configuration of an embodiment of the main body of the optical tomographic imaging system illustrated in FIG. 1.

FIG. 1 is a view illustrating a schematic configuration of an embodiment of the optical tomographic imaging system of the invention; FIG. 2 is a block diagram illustrating a schematic configuration of an embodiment of the main body of the optical tomographic imaging system illustrated in FIG. 1.

An optical tomographic imaging system 10 of the invention illustrated in FIG. 1 acquires a tomographic image of an object under measurement by a measuring method based upon optical coherence tomography or OCT. The optical tomographic imaging system 10 comprises:

a main body of the system 11 for acquiring and generating a tomographic image of the object under measurement, a given length of an optical probe 16 inserted into an endoscope 13 and comprising a rotary optical probe FB1 for transmitting the measuring light from the main body of the system 11 and the returning light from the object under measurement, an optical fiber cord 17 connected with the main body of the system 11 and having a stationary optical fiber FB2 for transmitting the measuring light and the returning light, an optical rotary adapter 18 provided between the optical probe 16 and the optical fiber cord 17 and used as a rotary drive unit for rotatably connecting the rotary optical fiber FB1 to the stationary optical fiber FB2 to transmit the measuring light and the returning light, and an extra length handling mechanism 15 for winding the optical probe 16 on the side thereof closer to the optical rotary adapter 18 into a circular loop 16a having at least a given minimum diameter and holding the optical probe 16 so wound.

As illustrated in FIG. 2, the main body of the system 11 comprises a light source unit 12 for emitting light La, a splitter/combiner 14 for splitting the light La emitted by the light source unit 12 into measuring light L1 and reference light L2 and combining returning light L3 from the object under measurement or the sample under test and the reference light L2 to produce interference light L4, an interference light detector 20 for detecting the interference light L4 produced by the splitter/combiner 14 as interference signal, a processor 22 for processing the interference signal detected by the interference light detector 20 to acquire an optical tomographic image (also referred to simply as "tomographic image" below), and a display 24 for displaying the tomographic image acquired by the processor 22.

The main body of the system 11 further comprises an optical path length adjuster 26 for adjusting the optical path length of the reference light L2, an optical fiber coupler 28 for splitting the light La emitted by the light source unit 12, a detector 30a for detecting the reference light L2 and a detector 30b for detecting the returning light L3, an operation control 32 for entering various conditions in the processor 22, the display 24, etc., and changing the settings, among other functions. In the optical tomographic imaging system 10 illustrated in FIG. 2, various light beams such as the emitted light La, the measuring light L1, the reference light L2, and the returning light L3 as described above are guided between the components such as optical devices, using various optical fibers FB (FB3, FB4, FB5, FB6, etc.) including the rotary optical fiber FB1 and the stationary optical fiber FB2 as optical transmission paths, as will be described later in detail.

First, the optical rotary adapter used for the optical tomographic imaging system 10 illustrated in FIGS. 1 and 2 will be described.

Figure 3:
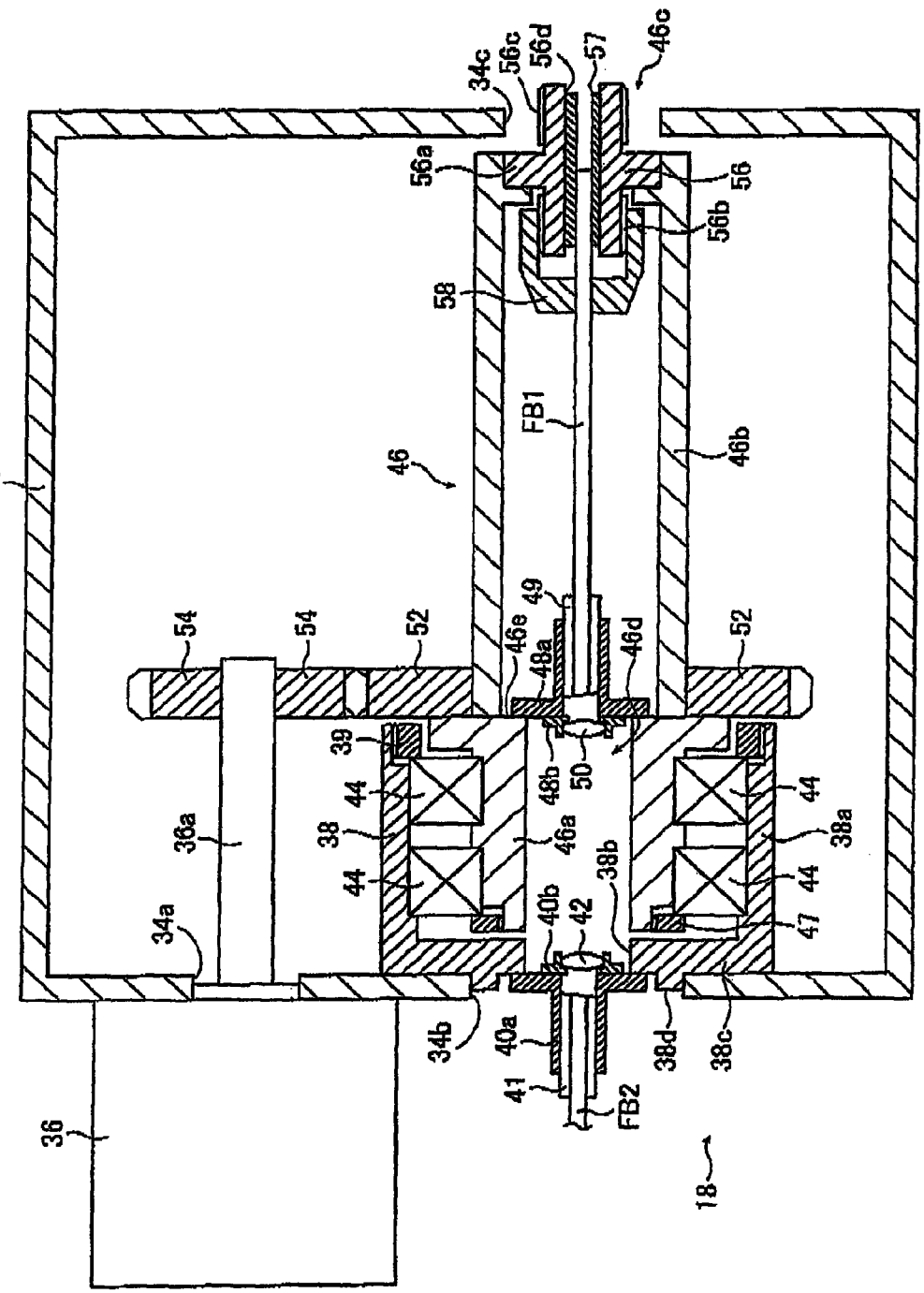
FIG. 3 is a schematic sectional view of an embodiment of the optical rotary adapter illustrated in FIG. 2.
Figure 4:
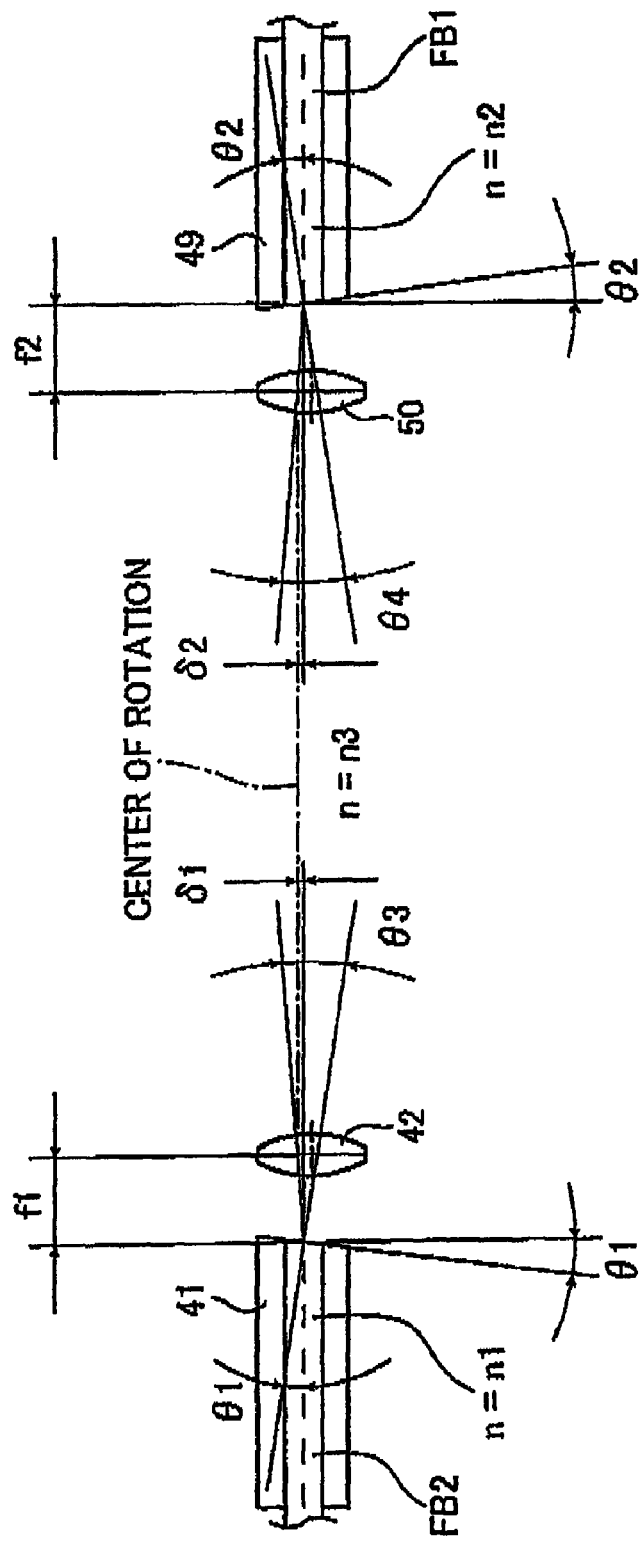
FIG. 4 is a view for explaining an example of the positional relationship of the optical fibers and the collimating lenses with respect to the center of rotation of the optical rotary adapter illustrated in FIG. 3.

FIG. 3 is a schematic sectional view of an embodiment of the optical rotary adapter illustrated in FIG. 2; FIG. 4 is a view for explaining an example of the positional relationship of optical fibers and collimating lenses with respect to the center of rotation of the optical rotary adapter illustrated in FIG. 3.

The optical rotary adapter 18 illustrated in FIG. 3 comprises a casing 34, a motor 36 mounted on the outside of the casing 34, a fixed sleeve 38 secured inside the casing 34, the stationary optical fiber FB2 and a stationary collimating lens 42 secured respectively via holders 40a and 40b that in turn are fixedly attached to one end face of the fixed sleeve 38, a rotary assembly 46 essentially composed of a mounting cylinder 46a rotatably carried by the fixed sleeve 38 by the intermediate of bearings 44 and a rotary assembly 46b integrated with the mounting cylinder 46a, the rotary optical fiber FB1 and a rotary collimating lens 50 secured respectively via holders 48a and 48b fixedly mounted at substantially the center of one end face of the mounting cylinder 46a, a gear 52 mounted on the periphery of the rotary cylinder 46b of the rotary assembly 46, and a gear 54 attached to a rotary shaft 36a of the motor 36 and meshing with the gear 52 of the rotary cylinder 46b.

The casing 34 houses components of the optical rotary adapter 18 except the motor 36, the holder 40a, the stationary optical fiber FB2, and some other components. The casing 34 is formed with an aperture 34a through which the rotary shaft 36a of the motor 36 passes; it is further formed with an aperture 34b for mounting the fixed sleeve 38 serving to secure the holder 40a holding the optical fiber FB2 and an aperture 34c allowing the optical fiber FB1 to pass rotatably therethrough. The aperture 34b and the aperture 34c are located opposite each other.

The motor 36 turns the rotary cylinder 46b to rotate the mounting cylinder 46a of the rotary assembly 46, thereby turning the FB1 carried substantially at the center of the mounting cylinder 46a and the rotary cylinder 46b. The motor 36 turns its rotary shaft 36a to rotate the gear 54 mounted at the tip of the rotary shaft 36a, the gear 52 of the rotary cylinder 46b meshing with the gear 54, and the rotary cylinder 46b, thus turning the mounting cylinder 46a of the rotary assembly 46. This causes the FB1 carried substantially at the center of the mounting cylinder 46a and the rotary cylinder 46b of the rotary assembly 46 to rotate.

The fixed sleeve 38 supports the stationary optical fiber FB2 and the stationary collimating lens 42 at their respective given locations and rotatably carries the mounting cylinder 46a of the rotary assembly 46. The fixed sleeve 38 is cylindrical and has a circular tubing section 38a opening on one end thereof and a discal section 38c having a central aperture 38b on the other end. The discal section 38c is attached to the inner wall of the casing 34 such that an annular ridge 38d formed on the outer face of the discal section 38c is fitted in the aperture 34b of the casing 34.

A flange section of the holder 40a is attached to the outside of the discal section 38c of the fixed sleeve 38 thus secured to the casing 34 in such a manner as to cover the central aperture 38b of the fixed sleeve 38.

The mounting cylinder 46a of the rotary assembly 46 is fitted in the circular tubing section 38a of the fixed sleeve 38 from the opening side thereof inwardly with two bearings 44 provided between the inner periphery of the circular tubing section 38a of the fixed sleeve 38 and the outer periphery of the cylindrical mounting cylinder 46a of the rotary assembly 46. The two bearings 44 are urged to the recess in the inner periphery of the circular tubing section 38a of the fixed sleeve 38 and obstructed by a ring 39 having a male thread section engaging the female thread section formed in the inner periphery of the opening end of the circular tubing section 38a to ensure that the bearings do not escape from the engagement with the inner periphery of the circular tubing section 38a toward the opening side.

The holder 40a is a flanged circular tubing member for holding centrally therein the optical fiber FB2 held by a cylindrical ferrule 41. The optical fiber FB2 held by the ferrule 41 is held by the holder 40a such that its end face is spaced a given distance from the flanged end face of the holder 40a. The holder 40a is attached, directed outwardly, to the external periphery of the central aperture 38b of the discal section 38c of the fixed sleeve 38 such that the central optical axis of the stationary optical fiber FB2 held by the holder 40a is located substantially at the center of the circular central aperture 38b of the fixed sleeve 38 or, specifically, in a position eccentric to the central aperture 38b by a given amount (slightly).

The optical fiber FB2 is incorporated in the optical fiber cord 17, which may be any known optical fiber cord.

The ferrule 41 has the optical fiber FB2 inserted therein to hold and protect the optical fiber FB2 and may typically be a zirconia ferrule or a metal ferrule formed of a metal such as nickel alloy.

The holder 40b is a flanged circular tubing member for holding the collimating lens 42 and its flange section is attached to the flange section of the holder 40a such that the center of the end face of the optical fiber FB2 and the center of the collimating lens 42 are spaced from each other on the optical axis thereof by a given distance, specifically by the focal distance of the collimating lens 42.

The optical axis of the optical fiber FB2 and the center of the collimating lens 42 are offset from each other to permit horizontal emission of light.

The stationary optical fiber FB2 transmits the measuring light L1 split by the splitter/combiner 14 to the rotary optical fiber FB1 and transmits the returning light L3 guided by the optical fiber FB1. The end face of the optical fiber FB2 and the end face of the ferrule 41 having the optical fiber FB2 inserted therein at the core are inclined end faces forming an identical plane inclined a given angle with respect to the plane perpendicular to the optical axis of the optical fiber FB2.

The stationary collimating lens 42 collimates the measuring light L1 emitted from the end of the optical fiber FB2 and allows the collimated light to enter the rotary collimating lens 50 and focuses the returning light L3 collimated and returned from the collimating lens 50 allowing the thus focused light to enter the optical fiber FB2. The end face of the optical-fiber FB2 and the collimating lens 42 are positioned such that the center of the inclined end face of the optical fiber FB2 and the center of the collimating lens 42 are spaced from each other on the optical axis thereof by a distance equal to the focal distance of the collimating lens 42.

The rotary assembly 46 has the mounting cylinder 46a provided on the forward end thereof (the left-hand side in FIG. 3) and the rotary cylinder 46b provided on the rear end thereof (the right-hand side in FIG. 3) integrated with each other such that these two components rotate as a single unit about an identical axis of rotation, the mounting cylinder 46a on the forward end being fitted into the circular tubing section 38a of the fixed sleeve 38 and rotatably carried by the fixed sleeve 38 by the intermediate of the two bearings 44. Thus, the rotary assembly 46 rotatably carries the rotary optical fiber FB1 held substantially at the center of the inside of the mounting cylinder 46a and the rotary cylinder 46b to permit rotation of the optical fiber FB1.

The mounting cylinder 46a of the rotary assembly 46 is a cylindrical member having a flanged end face 46e on its rear end whereas its forward end face is located opposite the discal section 38c of the fixed sleeve 38, with the two bearings 44 provided on the outer periphery of the mounting cylinder 46a. The mounting cylinder 46a provides the flanged end face 46e on its rear end for securing the optical fiber FB1 and the collimating lens 50 close to the center thereof and thus functions as a mounting cylinder for the optical fiber and the collimating lens whereas the end face of the rotary cylinder 46b is attached to the periphery of the flanged end face 46e.

In the rotary assembly 46, the two bearings 44 are press-fitted in the outer periphery of the mounting cylinder 46a so as to be urged into their respective recesses and secured by a ring 47 having a female thread section engaging the male thread section formed in the periphery of the opening end of the mounting cylinder 46*a* to ensure that the bearings do not escape from the engagement with the periphery of the mounting cylinder 46*a* toward the opening side.

The rotary cylinder 46*b* has an inner periphery having an inside diameter greater than that of the mounting cylinder 46*a* and having an outside diameter smaller than that of the flanged end face 46*e* of the mounting cylinder 46*a*. The forward end face of the rotary cylinder 46*b* is attached to the periphery of the flanged end face 46*e* on the rear end of the mounting cylinder 46*a* such that both share the same central axis of rotation, thus forming the rotary assembly 46 composed of the rotary cylinder 46*b* integrated with the mounting cylinder 46*a*.

There is formed between the mounting cylinder 46*a* and the rotary cylinder 46*b* a step by the flanged end face 46*e* of the mounting cylinder 46*a*. Against that step is abutted the gear 52 mounted on the periphery of the forward end of the rotary cylinder 46*b*. As the gear 52 turns, the rotary cylinder 46*b* rotates, causing the rotary assembly 46 and, hence, the mounting cylinder 46*a* forming part of the rotary assembly 46, to rotate.

At the rear end of the rotary cylinder 46*b*, there is provided a connecting unit 46*c* substantially on the central axis thereof. The connecting unit 46*c* is provided to support the inclined rear end face of the optical fiber FB1 attached to the mounting cylinder 46*a* so as to lie substantially on the central axis thereof and connect the optical fiber FB1 thus held inside the rotary cylinder 46*b* to the optical fiber FB1 in the optical probe 16.

Note that the rotary assembly 46 may be configured such that it may be disassembled into the mounting cylinder 46*a* and the rotary cylinder 46*b* by disengaging the forward end face of the rotary cylinder 46*b* from the flanged rear end face 46*e* of the mounting cylinder 46*a*.

The flange section of the holder 48*a* is attached closer to the center of the flanged rear end face 46*e* of the mounting cylinder 46*a* of the rotary assembly 46 in such a manner as to cover the central aperture 46*d* of the mounting cylinder 46*a*.

The holder 48*a*, as is the holder 40*a*, is a flanged circular tubing member for holding centrally therein the optical fiber FB1 held by a cylindrical ferrule 49. The optical fiber FB1 held by the ferrule 49 is held by the holder 48*a* such that its forward end face is spaced a given distance from the flanged end face of the holder 48*a*. The holder 48*a* is attached, directed outwardly, to the periphery of the central aperture 46*d* of the flanged end face 46*e* such that the central optical axis of the rotary optical fiber FB1 held by the holder 48*a* is located substantially at the center of the central aperture 46*d* of the mounting cylinder 46*a* or, to be more specific, in an offset (eccentric) position by a given amount (slightly) from the center of rotation of the mounting cylinder 46*a* (rotary assembly 46).

The ferrule 49 having the optical fiber FB1 inserted therein at the core has a function to hold and protect the optical fiber FB1 and may, as with the ferrule 41, typically be a zirconia ferrule or a metal ferrule formed of a metal such as nickel alloy.

The holder 48*b* is, as is the holder 40*b*, a flanged circular tubing member for holding the collimating lens 50, and its flange section is attached to the flange section of the holder 48*a* such that the center of the forward end face of the optical fiber FB1 and the center of the collimating lens 50 are spaced from each other on the optical axis thereof by a given distance, specifically by the focal distance of the collimating lens 50.

Note that the optical axis of the optical fiber FB1 and the center of the collimating lens 50 are provided in an offset positional relationship permitting horizontal emission of light beam.

The rotary optical fiber FB1 guides the measuring light L1 transmitted from the stationary optical fiber FB2 to the object under measurement and guides and transmits the returning light L3 from the object under measurement to the stationary optical fiber FB2. The forward end face of the optical fiber FB1 and the forward end face of the ferrule 49 having the optical fiber FB1 inserted therein at the core are inclined end faces forming an identical plane inclined a given angle with respect to the plane perpendicular to the optical axis of the optical fiber FB1.

The stationary collimating lens 50 focuses the measuring light L1 collimated by the collimating lens 42 and allows the focused light to enter the optical fiber FB1; it also collimates the returning light L3 emitted from the forward end of the optical fiber FB1 and allows the thus collimated light to enter the stationary collimating lens 42. The forward end face of the optical fiber FB1 and the collimating lens 50 are positioned such that the center of the inclined end face of the optical fiber FB1 and the center of the collimating lens 42 are spaced from each other on the optical axis by a distance equal to the focal distance of the collimating lens 50.

As described earlier, the connecting unit 46*c* attached to the rear end face of the rotary cylinder 46*b* of the rotary assembly 46 is provided to support the inclined rear end face of the optical fiber FB1 attached to the mounting cylinder 46*a* substantially on the central axis thereof and held substantially on the central axis of the rotary cylinder 46*b* and connect the optical fiber FB1 held inside the rotary cylinder 46*b* to the optical fiber FB1 in the optical probe 16.

The connecting unit 46*c* comprises an end face member 56 and a cap nut 58. The end face member 56 includes a flange section 56*a* fitted in the rear end face of the rotary cylinder 46*b* so as to abut against the step formed in the inner periphery thereof, male thread sections 56*b* and 56*c* provided on the opposite sides of the flange section 56*a*, and a central through-hole 56*d* in which the optical fiber FB1, which is held substantially at the center of the mounting cylinder 46*a* by the holder 48*a* by the intermediate of the ferrule 49, is inserted substantially along the central axis of rotation and held in position by the intermediate of a split sleeve 57. The cap nut 58 includes a central opening for passing the optical fiber FB1 therethrough, a female thread section engaging the male thread section 56*b* of the end face member 56, and a through-hole for passing the optical fiber FB1 that is inserted in the central through-hole 56*d*. The end face member 56 of the connecting unit 46*c*, in particular the male thread section 56*c*, functions as a fiber connector for attaching the optical fiber FB1 in the optical probe 16 to the rotary adapter 18.

While the optical fiber FB1, with its inclined forward end face held by the holder 48*a* located in the position as shown, is disposed substantially at the center of the mounting cylinder 46*a* and the rotary cylinder 46*b* such that the optical axis of the optical fiber FB1 and the central axis of rotation of the mounting cylinder 46*a* are offset from each other by a given amount in the illustrated example, it is preferable that the optical fiber FB1 is supported at the center of the rotary cylinder 46*b* by the end face member 56 and the cap nut 58 such that in the connecting unit 46*c* at the rear end, the optical axis of the optical fiber FB1 and the central axis of rotation of the rotary cylinder 46*b* coincide with each other.

The male thread section 56*c* of the connecting unit 46*c* of the rotary cylinder 46*b* is located at the aperture 34*c* of the casing 34 and serves as a connector to optically connect the optical fiber FB1 in the optical probe 16 to the optical fiber FB1 in the rotary assembly 46. The connecting unit 46c may be coupled with a variety of optical connectors including normal optical connectors such as an SC connector, an FC connector, and optical connectors of physical contact type.

Thus, in the optical tomographic imaging system 10 of the invention, connection and disconnection between the stationary optical fiber FB2 directly connected to the main body of the system 11 with an optical connector such as an FC connector and the optical fiber FB1 encased in the optical probe 16 is achieved preferably by providing the connecting unit 46c of the rotary assembly 46 in the optical rotary adapter 18 as a connecting unit for an optical connector and having an optical connector attached to the terminal of the optical fiber FB1 encased in the optical probe 16 to permit connection and disconnection between the connecting unit 46c and the optical connector attached to the terminal of the optical fiber FB1.

As will be described later herein, the optical fiber FB1 in the optical probe 16 is clothed with a spring or the like to protect the optical fiber FB1 and hold it rotatable with a degree of flexibility.

The optical rotary adapter 18 permits removal of the rotary assembly 46, with the holder 48a holding the optical fiber FB1 attached, by withdrawing the rotary assembly 46 from the fixed sleeve 38 with the holder 40a holding the optical fiber FB2 attached, by removing, for example, the rotary cylinder 46b of the rotary assembly 46 and the gear 52 to remove the ring 39, although this may not be readily achieved because of the press-fitted bearings 44. In the process, the two bearings 44 are withdrawn from the inner periphery of the fixed sleeve 38 together with the mounting cylinder 46a of the rotary assembly 46.

In this procedure, the collimating lenses 50 and 42 each attached adjacent the end of the respective optical fibers FB1 and FB2 prevent accidental damage or break of the connecting ends of the optical fibers FB1 and FB2.

While the connecting unit 46c of the rotary cylinder 46b of the rotary assembly 46 functions as a connector for the optical fiber according to the configuration of the illustrated example, an alternative configuration may be used where the optical fiber FB1 is only held in position by the holder 48a attached to the mounting cylinder 46a, allowing the optical fiber FB1 thus held to extend all the way through the tip of the optical probe 16.

According to the optical rotary adapter 18, the optical axes of the optical fibers FB1 and FB2 are offset from the center of rotation of the optical fiber FB1, i.e., the center of rotation of the rotary assembly 46 (mounting cylinder 46a), in order to reduce the attenuation of the returning light L3 from the object under measurement for improved signal-to-noise ratio of the returning light L3.

FIG. 4 is a schematic view illustrating the positional relationship between the stationary optical transmission system composed of the stationary optical fiber FB2 and the stationary collimating lens 42 and the rotary optical transmission system composed of the rotary optical fiber FB1 and the rotary collimating lens 50.

Now, as illustrated in FIG. 4, let θ1 be the inclination angle of the inclined end face of the stationary optical fiber FB2 with respect to a plane perpendicular to the optical axis thereof, n1 the refractive index of the optical fiber FB2, n3 the refractive index of the medium between the optical fibers FB2 and FB1 that propagates the light excluding the collimating lenses 42 and 50, and θ3 the angle (refracting angle) of the light traveling inside the optical fiber FB2 in the direction parallel to the optical axis thereof and refracted at the interface between the inclined end face of the optical fiber FB2 and the medium with respect to the normal line to the inclined end face, and suppose that the distance along the optical axis between the center of the inclined end face of the optical fiber FB2 and the center of the collimating lens 42 is equal to the focal distance f1 of the collimating lens 42 on the assumption that the collimating lens 42 is a thin sheet lens. Then, the stationary optical fiber FB2 and the collimating lens 42 are preferably mounted to the mounting cylinder 46a such that the offset amount δ1 between the optical axis of the optical fiber FB2 and the central axis of rotation of the rotary assembly 46 (mounting cylinder 46a) satisfies the following expressions (1) and (2).

$$n1 \times \sin θ1 = n3 \times \sin θ3 \quad (1)$$

$$δ1 = f1 \times \tan(θ3 - θ1) \quad (2)$$

Likewise, as illustrated in FIG. 4, let θ2 be the inclination angle of the inclined forward end face of the rotary optical fiber FB1 with respect to the plane perpendicular to the optical axis thereof, n2 the refractive index of the optical fiber FB1, n3 the refractive index of the above medium propagating the light, and θ4 the angle (refracting angle) of the light traveling inside the optical fiber FB1 in the direction parallel to the optical axis thereof and refracted at the interface between the inclined end face and the medium with respect to the normal line to the inclined end face, and suppose that the distance along the optical axis between the center of the inclined end face of the optical fiber FB1 and the center of the collimating lens 50 is equal to the focal distance f2 of the collimating lens 50 on the assumption that the collimating lens 50 is a thin sheet lens. Then, the rotary optical fiber FB1 and the collimating lens 50 are preferably mounted to the mounting cylinder 46a such that the offset amount δ2 between the optical axis of the optical fiber FB1 and the central axis of rotation of the rotary assembly 46 (mounting cylinder 46a) satisfies the following expressions (3) and (4).

$$n2 \times \sin θ2 = n3 \times \sin θ4 \quad (3)$$

$$δ2 = f2 \times \tan(θ4 - θ2) \quad (4)$$

As described above, the provision of the stationary optical transmission system composed of the stationary optical fiber FB2 and the stationary collimating lens 42 and the rotary optical transmission system composed of the rotary optical fiber FB1 and the rotary collimating lens 50 illustrated in FIG. 4 lessens the attenuation of the returning light L3 from the object under measurement to reduce white noise and improve the signal-to-noise ratio of the returning light L3.

Preferably, the stationary optical transmission system composed of the stationary optical fiber FB2 and the stationary collimating lens 42 and the rotary optical transmission system composed of the rotary optical fiber FB1 and the rotary collimating lens 50 illustrated in FIG. 4 are disposed so as to be in a symmetric, i.e., a line-symmetric position with respect to each other.

In that case, both transmission systems will share the refractive index (n1=n2), the inclination angle (θ1=θ2), the refracting angle (θ3=θ4), the focal distance (f1=f2), and the offset amount (δ1=δ2).

Now, for example, in FIG. 4, let the refractive index n1 of the optical fiber FB2 be 1.5, its inclination angle θ1 be 8°, and the refractive index n3 of the medium be 1.0 assuming that it is air. Then, the refracting angle θ3 is 12° from the above expression (1). Therefore, when the focal distance f1 of the collimating lens 42 is 2 mm, the above expression (2) gives an offset amount δ1 of 0.14 mm between the optical axis of the optical fiber FB2 and the central axis of rotation. Accordingly, where said two transmission systems are disposed symmetrically, the holders 40a and 48a holding the respective optical fibers FB1 and FB2 may be disposed in such a position with respect to the fixed sleeve 38 and the mounting cylinder 46a, respectively, that the optical axes of the optical fibers FB1 and FB2 are offset from the central axis of rotation by 0.14 mm.

The optical rotary adapter 18 is basically configured as described above.

While the rotary drive unit of the optical tomographic imaging system 10 is embodied by the optical rotary adapter 18 in the illustrated example, the invention is not limited thereto; one may use any known rotary drive unit used for optical tomographic imaging systems, provided that the rotary drive unit is capable of rotatably and detachably connecting the rotary optical fiber encased in the optical probe to the stationary optical fiber in the optical fiber cord to permit transmission of the measuring light and the returning light. For example, one may use the optical connector of the optical probe as combined with the rotary drive unit (rotary connector) disclosed in JP 2006-215005 A filed by one of the Applicants of the present application or the optical rotary joint disclosed in JP 2000-131222 A.

Next, the optical probe 16 will be described.

The optical probe 16 is connected with the optical rotary adapter 18 (a connecting unit 46c of the rotary assembly 46, see FIG. 3) as illustrated in FIGS. 1 and 2; the optical probe 16 is wound, on the side thereof connected to the optical rotary adapter 18, into a circular loop 16a having at least a given minimum diameter in the extra length handling mechanism 15 and held so wound. The extra length handling mechanism 15 and the circular loop 16a of the optical probe 16 will be described later in detail.

The optical probe 16 having the optical fiber FB1 incorporated therein is connected via the optical rotary adapter 18 to the optical fiber cord 17 having the optical fiber FB2 incorporated therein such that the measuring light L1 is delivered from the optical fiber FB2 to the optical fiber FB1 through the optical rotary adapter 18; the measuring light L1 is then further transmitted by the optical fiber FB1 to irradiate the object under measurement S and acquire the returning light L3 from the object under measurement S; and the returning light L3 thus acquired is transmitted by the optical fiber FB1 to the optical fiber FB2 through the optical rotary adapter 18.

Figure 5:
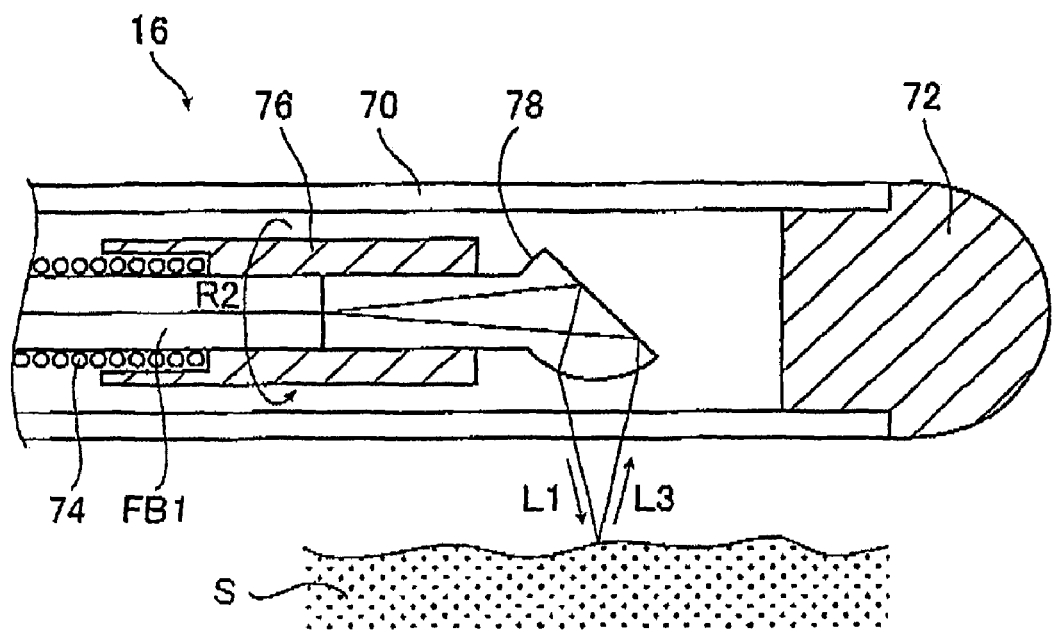
FIG. 5 is a partial, sectional view illustrating an embodiment of an optical probe used for the optical tomographic imaging system of FIG. 2, with the tip of the optical probe shown enlarged.

As illustrated in FIG. 5, the optical probe 16 comprises a probe sheath 70, a cap 72, an optical fiber FB1, a spring 74, a mounting member 76, and an optical lens 78.

The probe sheath 70 is a cylindrical member having a flexibility and formed of a material permitting transmission of the measuring light L1 and the returning light L3. The probe sheath 70 has at least part thereof close to its tip, i.e., an end thereof at which the measuring light L1 and the returning light L3 pass the probe sheath 70 (the end being opposite from the optical fiber FB1, referred to as "the tip of the probe sheath 70" below), formed all the way around circumferentially of a material permitting transmission of light (transparent material).

The cap 72 is provided on the tip of the probe sheath 70 to close the tip of the probe sheath 70.

The optical fiber FB1 is a linear member and encased in the probe sheath 70 along the length thereof; it guides the measuring light L1 delivered from the optical fiber FB2 through the optical rotary adapter 18 to an optical lens 78 and guides the returning light L3 from the object under measurement S acquired by the optical lens 78 by irradiating the object under measurement S with the measuring light L1 to the optical rotary adapter 18, the returning light L3 then entering the optical fiber FB2.

The optical fiber FB1 and the optical fiber FB2 are connected by the optical rotary adapter 18; they are optically connected such that the rotation of the optical fiber FB1 is not conveyed to the optical fiber FB2. The optical fiber FB1 is provided rotatably in relation to the probe sheath 70.

The spring 74 is secured to the periphery of the optical fiber FB1. The optical fiber FB1 and the spring 74 are connected to the optical rotary adapter 18.

The optical lens 78 is disposed at the measuring end of the optical fiber FB1 (the end of the optical fiber FB1 opposite from the optical rotary adapter 18) and has an end formed to have a substantially spherical shape to focus the measuring light L1 delivered from the optical fiber FB1 onto the object under measurement S.

The optical lens 78 irradiates the object under measurement S with the measuring light L1 delivered from the optical fiber FB1 and directs the returning light L3 from the object under measurement S to the optical fiber FB1.

The mounting member 76 is disposed on the periphery over the joint between the optical fiber FB1 and the optical lens 78 to secure the optical lens 78 to the end of the optical fiber FB1. The mounting member 76 may secure the optical fiber FB1 and the optical lens 78 by any of the methods including but not limited to a method using an adhesive material to bond the mounting member 76 to the optical fiber FB1 and the optical lens 78 and a method using a mechanical structure including bolts. The mounting member 76, as with the ferrules 41 and 49 described earlier, may be any appropriate member such as a zirconia ferrule or a metal ferrule used for securing, holding and protection.

As described above, the optical fiber FB1 and the spring 74 are connected to the rotary assembly 46 (the connecting unit 46c of the rotary cylinder 46b) of the optical rotary adapter 18, and rotation of the optical fiber FB1 and the spring 74 by means of the rotary cylinder 46b causes the optical lens 78 to turn in relation to the probe sheath 11 in the direction indicated by the arrow R2 in FIG. 4. The optical rotary adapter 18 has a rotary encoder (not shown) to detect the irradiation position of the measuring light L1 according to the position information (angular information) on the optical lens 78 based on the signal given by the rotary encoder. That is, the measuring position is determined by detecting the angle of the rotating optical lens 78 with respect to a reference position in the direction of rotation.

As the optical rotary adapter 18 turns the optical fiber FB1 and the spring 74 in the direction indicated by the arrow R2 in FIG. 5, the optical probe 16, configured as described above, irradiates the object under measurement S with the measuring light L1 emitted from the optical lens 78 by scanning in the direction indicated by the arrow R2 (in the circumferential direction of the probe sheath 70) and acquires the returning light L3.

Thus acquired is the returning light L3 for the whole circumference of the probe sheath 70 as it is reflected by the object under measurement S.

Now, description will be made of the components of the main body 11 of the optical tomographic imaging system 10 illustrated in FIG. 2.

As illustrated in FIG. 2, the light source unit 12 comprises a semiconductor optical amplifier 60, an optical splitter 62, a collimating lens 64, a diffraction grating element 66, an optical system 67, and a rotary polygon mirror 68 and emits laser beam La that is frequency-swept with a constant period.

The semiconductor optical amplifier (semiconductor gain medium) 60 emits feeble light upon application of drive current and amplifies incoming light. The semiconductor optical amplifier 60 is connected with an optical fiber FB10. More specifically, one end of the optical fiber FB10 is connected to a part of the semiconductor optical amplifier 60 at which light is emitted, whereas the other end of the optical fiber FB10 is connected to a part of the semiconductor optical amplifier 60 at which light enters. The light emitted from the semiconductor optical amplifier 60 is emitted to the optical fiber FB10 and re-enters the semiconductor optical amplifier 60.

Thus, the semiconductor optical amplifier 60 and the optical fiber FB10, forming an optical path loop, provide an optical resonator. Application of activating electric current to the semiconductor optical amplifier 60 causes a laser beam in the form of pulse to be generated.

The optical splitter 62 is provided on the optical path of the optical fiber FB10 and also connected with an optical fiber FB11. The optical splitter 62 directs part of the light guided through the optical fiber FB10 to the optical fiber FB11.

The collimating lens 64 is disposed at the other end of the optical fiber FB11, i.e., the end thereof not connected with the optical fiber FB10, and collimates the light emitted from the optical fiber FB11.

The diffraction grating element 66 is disposed with a given inclination angle on the optical path of the parallel light produced by the collimating lens 64. The diffraction grating element 66 disperses the parallel light emitted from the collimating lens 64.

The optical system 67 is disposed on the optical path of the light dispersed by the diffraction grating element 66. The optical system 67 comprises a plurality of lenses to refract the light dispersed by the diffraction grating element 66 and collimate the refracted light.

The polygon mirror 68 is disposed on the optical path of the parallel light produced by the optical system 67 to reflect the parallel light. The polygon mirror 68 is a rotary unit that turns at a constant speed in the R1 direction indicated in FIG. 2. It has the shape of a regular octagon in a plane perpendicular to the axis of rotation thereof and comprises lateral planes (planes forming the sides of the octagon) irradiated with the parallel light each formed with reflection surfaces for reflecting the light irradiating the planes.

The polygon mirror 68 turns to vary the angle of the reflection surfaces with respect to the optical axis of the optical system 67.

The light emitted from the optical fiber FB11 passes through the collimating lens 64, the diffraction grating element 66, and the optical system 67 and is reflected by the polygon mirror 68. The reflected light passes through the optical system 67, the diffraction grating element 66, and the collimating lens 64 and enters the optical fiber FB11.

Since the angle of the reflection surfaces of the rotary polygon mirror 68 varies with respect to the optical path of the optical system 67 as described above, the angle at which the rotary polygon mirror 68 reflects the light varies with time. Accordingly, only the light having a particular frequency range out of the light dispersed by the diffraction grating element 66 re-enters the optical fiber FB11. Thus, since the light having a particular frequency range entering the optical fiber FB11 is determined by the angle formed by the optical axis of the optical system 67 and the reflection surface of the rotary polygon mirror 68, the frequency range of the light entering the optical fiber FB11 varies with the angle formed by the optical axis of the optical system 67 and the reflection surface of the rotary polygon mirror 68.

The light having a particular frequency range allowed to enter the optical fiber FB11 is delivered through the optical coupler 62 to the optical fiber FB10 and combined with the light of the optical fiber FB10. Thus, the laser beam in the form of pulse guided to the optical fiber FB10 becomes a laser beam having a particular frequency range and this laser beam La having a particular frequency range is emitted to the optical fiber FB3.

Since the polygon mirror 68 is turning at a constant speed in the direction indicated by the arrow R1, the wavelength λ of the light re-entering the optical fiber FB11 varies with a constant period as time passes. Accordingly, the frequency of the laser beam La emitted to the optical fiber FB3 also varies with a constant period as time passes.

The light source unit 12 is configured as described above and emits the wavelength-swept laser light La to the optical fiber FB3.

Next, the splitter/combiner 14 is composed, for example, of a 2×2 optical fiber coupler and optically connected with the optical fiber FB2, the optical fiber FB3, the optical fiber FB4, and the optical fiber FB5.

The splitter/combiner 14 splits the incoming light La delivered from the light source unit 12 through the optical fiber FB3 into the measuring light L1 and the reference light L2, directing the measuring light L1 to the optical fiber FB2 and the reference light L2 to the optical fiber FB5.

Further, the splitter/combiner 14 combines the reference light L2, which enters the optical fiber FB5, undergoes frequency shift and optical path length modification effected by an optical path length adjuster 26 to be described, and returns through the optical fiber FB5 to enter the splitter/combiner 14, with the returning light L3 from the object under measurement S, which is acquired by an optical probe to be described and enters the splitter/combiner 14 through the optical fiber FB2. The splitter/combiner 14 emits the combined light to the optical fiber FB4.

The optical path length adjuster 26 is disposed on the emission side of the optical fiber FB5 from which the reference light L2 is emitted (i.e., at the end of the optical fiber FB5 opposite from the splitter/combiner 14).

The optical path length adjuster 26 comprises a first optical lens 80 for collimating the light emitted from the optical fiber FB5, a second optical lens 82 for focusing the light collimated by the first optical lens 80, a reflecting mirror 84 for reflecting the light focused by the second optical lens 82, a base 86 for supporting the second optical lens 82 and the reflecting mirror 84, and a mirror moving mechanism 88 for moving the base 86 in the direction parallel to the optical axis. The optical path length adjuster 26 adjusts the optical path length of the reference light L2 by varying the distance between the first optical lens 80 and the second optical lens 82.

The first optical lens 80 collimates the reference light L2 emitted from the core of the optical fiber FB5 and focuses the reference light L2 reflected by the reflecting mirror 84 onto the core of the optical fiber FB5.

The second optical lens 82 focuses the reference light L2 collimated by the first optical lens 80 onto the reflecting mirror 84 and collimates the reference light L2 reflected by the reflecting mirror 84. Thus, the first optical lens 80 and the second optical lens 82 form a confocal optical system.

The reflecting mirror 84 is disposed at the focal point of the light focused by the second optical lens 82 and reflects the reference light L2 focused by the second optical lens 82.

Thus, the reference light L2 emitted from the optical fiber FB5 is collimated by the first optical lens 80 and focused by the second optical lens 82 onto the reflecting mirror 84. Subsequently, the reference light L2 reflected by the reflecting mirror 84 is collimated by the second optical lens 82 and focused by the first optical lens 80 onto the core of the optical fiber FB5.

The base 86 fixedly holds the second optical lens 82 and the reflecting mirror 84 in position while the mirror moving mechanism 88 moves the base 86 in the direction of the optical axis of the first optical lens 80 (the direction indicated by the arrow A in FIG. 2).

The movement of the base 86 effected by the mirror moving mechanism 88 in the direction indicated by the arrow A changes the distance between the first optical lens 80 and the second optical lens 82, permitting the adjustment of the optical path length of the reference light L2.

The interference light detector 20 is connected with the optical fiber FB4 and detects as interference signal the interference light L4 produced by the splitter/combiner 14 by combining the reference light L2 and the returning light L3.

The optical tomographic imaging system 10 comprises the optical fiber coupler 28 for splitting the laser beam La from the optical fiber FB3 and directing the split laser beam La to the optical fiber FB6, the detector 30a provided on the optical path of the optical fiber FB6 split from the optical fiber coupler 28 for detecting the optical intensity of the split laser beam, and the detector 30b disposed on the optical path of the optical fiber FB4 for detecting the optical intensity of the interference light L4.

The interference light detector 20 adjusts the balance of the optical intensity of the interference light L4 detected from the optical fiber FB4 according to the results of the detection performed by the detector 30a and the detector 30b.

From the interference signal detected by the interference light detector 20, the processor 22 detects the area where the optical probe 16 in the measuring position is in contact with the object under measurement S or, more precisely, the area where the surface of the probe sheath 70 may be considered to be in contact with the surface of the object under measurement S, and acquires a tomographic image from the interference signal detected by the interference light detector 20.

Figure 6:
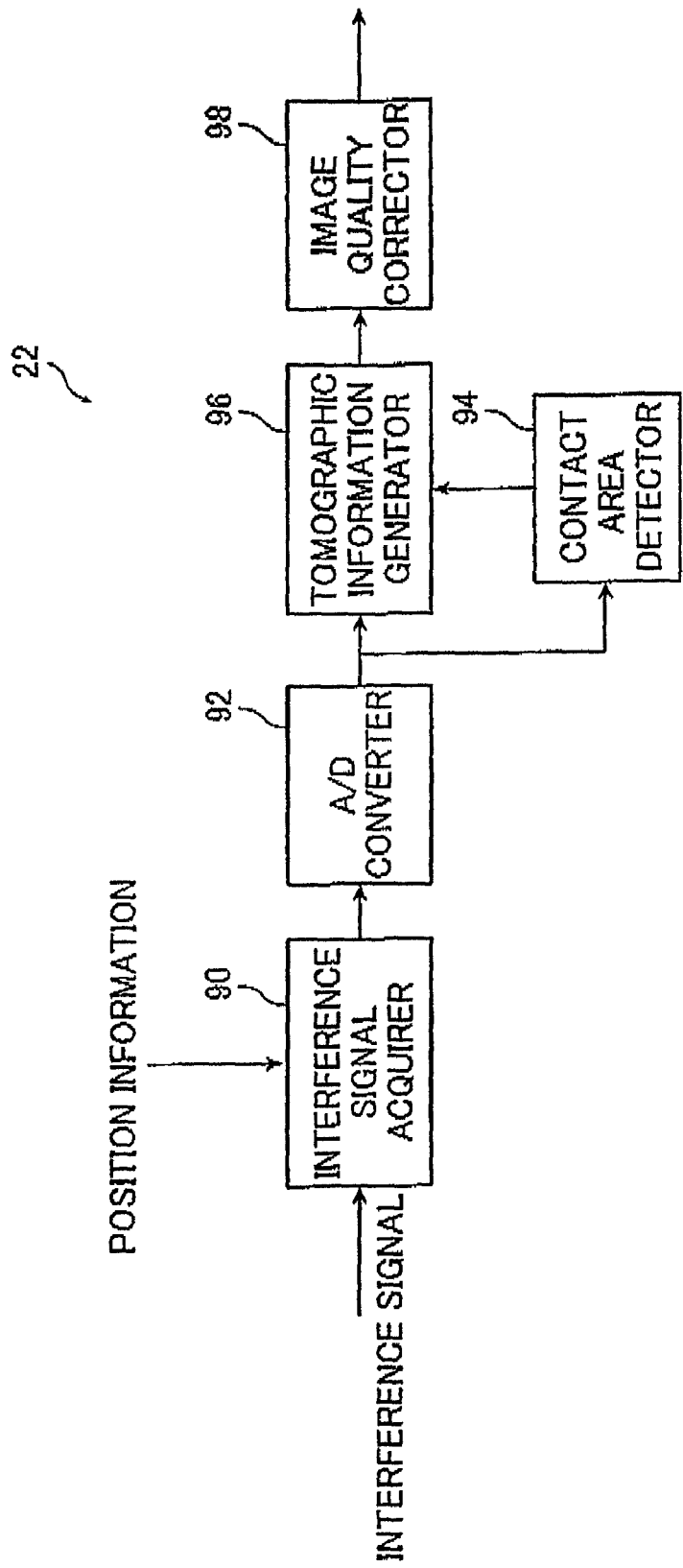
FIG. 6 is a block diagram illustrating a schematic configuration of an embodiment of the processor in the optical tomographic imaging system of FIG. 2.

As illustrated in FIG. 6, the processor 22 comprises an interference signal acquirer 90, an analog-to-digital converter 92, a contact area detector 94, a tomographic information generator 96, and an image corrector 98.

The interference signal acquirer 90 acquires the interference signal detected by the interference light detector 20 and acquires information on a measuring position detected by the optical rotary adapter 18, more specifically, position information on the measuring position detected from the information on a position of the optical lens 78 in the rotating direction, and correlates the interference signal with the position information on the measuring position.

The interference signal correlated with the position information on the measuring position is sent to the analog-to-digital converter 92.

The analog-to-digital converter 92 converts to digital signal the interference signal produced from the interference signal acquirer 90 as analog signal correlated with the position information on the measuring position.

The interference signal now correlated with the position information on the measuring position and converted to digital signal is sent to the contact area detector 94 and the tomographic information generator 96.

The contact area detector 94 applies fast Fourier transform (FFT) to the interference signal now converted to digital signal by the analog-to-digital converter 92 to acquire the relationship between frequency component and intensity of the interference signal and associates the frequency component, which is now correlated with the intensity, with the depth direction (the direction in which the distance from the center of rotation increases) to acquire information on the relationship between depth direction and intensity. From the information on the relationship between depth direction and intensity, the contact area detector 94 detects the position on the surface of the probe sheath 70 at which the measuring light L1 is transmitted and the contact area between that position on the surface of the probe sheath 70 at which the measuring light L1 is transmitted and the object under measurement S.

Thus, information on the contact area between the probe sheath 70 and the object under measurement S is sent to the tomographic information generator 96.

The tomographic information generator 96 processes the information on the relationship between frequency component and intensity obtained by fast Fourier transform applied to the interference signal converted to digital signal by the analog-to-digital converter 92 to acquire a depthwise tomographic image.

The tomographic information generator 96 only acquires a tomographic image from the interference signal of the information on a position judged to be the contact area from among the contact area information sent from the contact area detector 94 and acquires no tomographic image from an interference signal of the information on a position representing an area other than the contact area, that is, performs no FFT or no image acquisition processing from the results obtained by application of FFT, performing instead a masking process.

Now, description will be briefly made on the generation of an image performed by the tomographic information generator 96. Let S(1) be the optical intensity of interference fringes for each optical path length difference l of the various optical path length differences with which the returning light L3 from the respective depths in the object under measurement S interferes with the reference light L2 as the measuring light L1 irradiates the object under measurement S. Then, the optical intensity I(k) of the interference signal detected in the interference light detector 20 is expressed by an expression:

$$I(k) = \int_0^\infty S(1)[1 + \cos(k1)] dl$$

where k is the number of waves and l the optical path length difference. The above expression may be considered to represent an interferogram for a frequency range having the number of waves k=ω/c as a variable. Accordingly, applying fast Fourier transfer to the spectral interference fringes detected by the interference light detector 20 and determining the optical intensity S(1) of the interference light L4 in the tomographic information generator 96 yield information on the distance from the measurement starting position of the object under measurement S and reflection intensity information, thereby generating a tomographic image.

The image corrector 98 performs logarithmic conversion and radial conversion of the tomographic image generated by the tomographic information generator 96 to obtain a circular image centering about the center of rotation of the optical lens 78.

The image corrector 98 further performs sharpening processing, smoothing processing and the like on the tomographic image to correct the image quality.

The image corrector 98 sends the tomographic image with image quality corrected to the display 24.

The tomographic image may be sent at any appropriate timing; it may be sent to the display each time processing for one scan line is completed to effect rewrite each time one scan line is provided, or may be sent when processing for all the scan lines is completed (that is, when processing is completed to acquire an image as the optical lens has completed its one full rotation) to generate a circular tomographic image.

The display 24, which may be a CRT, a liquid crystal display device or the like, displays the tomographic image sent from the image corrector 98.

The operation control 32 comprises entry means such as a keyboard and a mouse, and control means for controlling various conditions according to the entered information and is connected to the processor 22 and the display 24. The operation control 32 performs, among others, entry, setting and change of thresholds, various processing conditions, etc. in the processor 22 and change of display settings in the display 24 according to the operator instructions entered at the entry means. The operation screen for the operation control 32 may be given on the display 24 or may be displayed on a separately provided monitor. The operation control 32 may be adapted to perform operation controls and settings of various conditions for the light source unit 12, the optical rotary adapter 18, the interference light detector 20, the optical path length adjuster 26 and the detectors 30a and 30b.

The main body 11 of the inventive optical tomographic imaging system 10 is basically configured as described above.

Now, the extra length handling mechanism 15, a dominant feature of the present invention, will be described.

Figure 7:
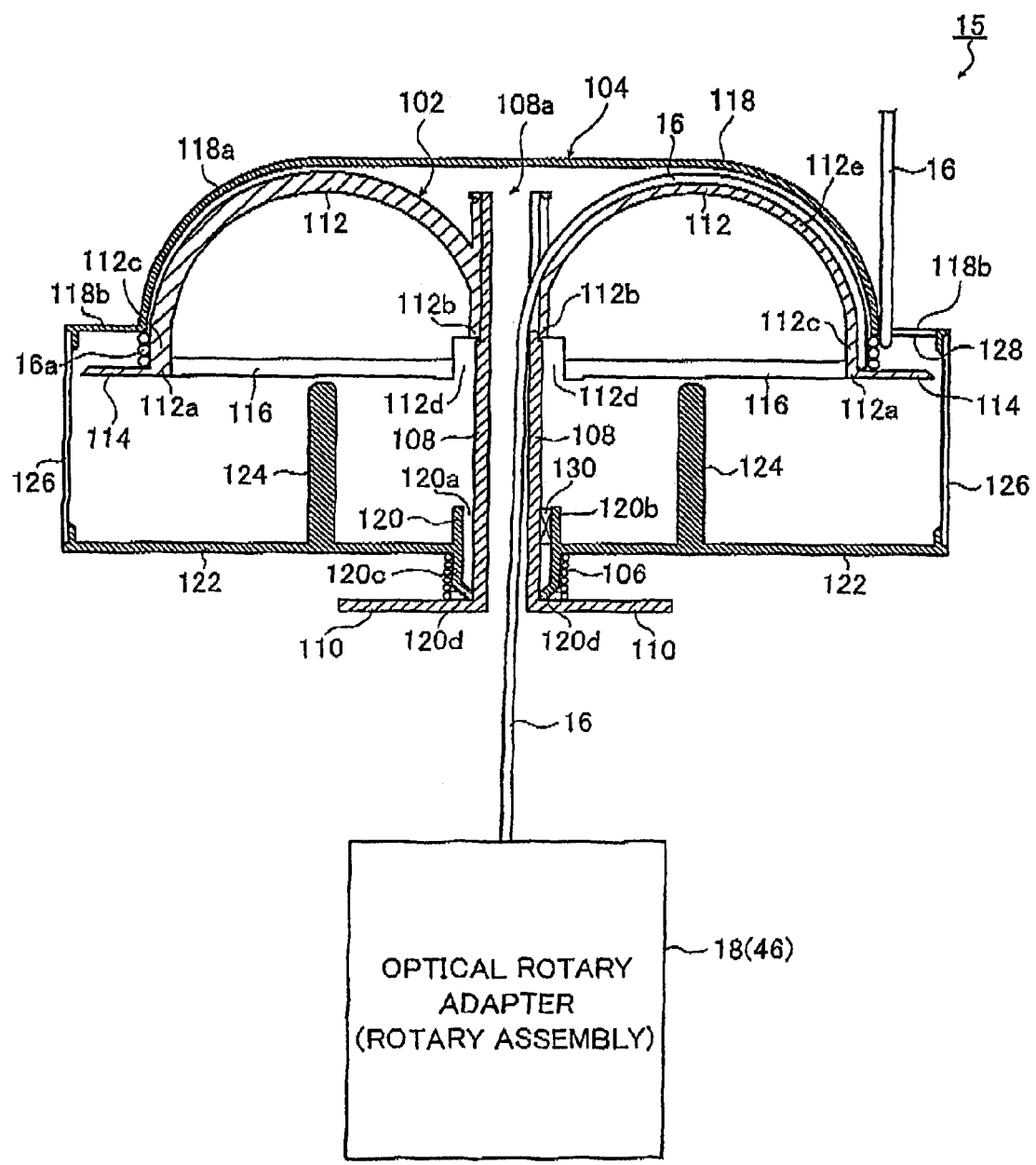
FIG. 7 is a sectional view of a schematic configuration of an embodiment of an extra length handling mechanism of the optical tomographic imaging system of FIG. 1.
Figure 8:
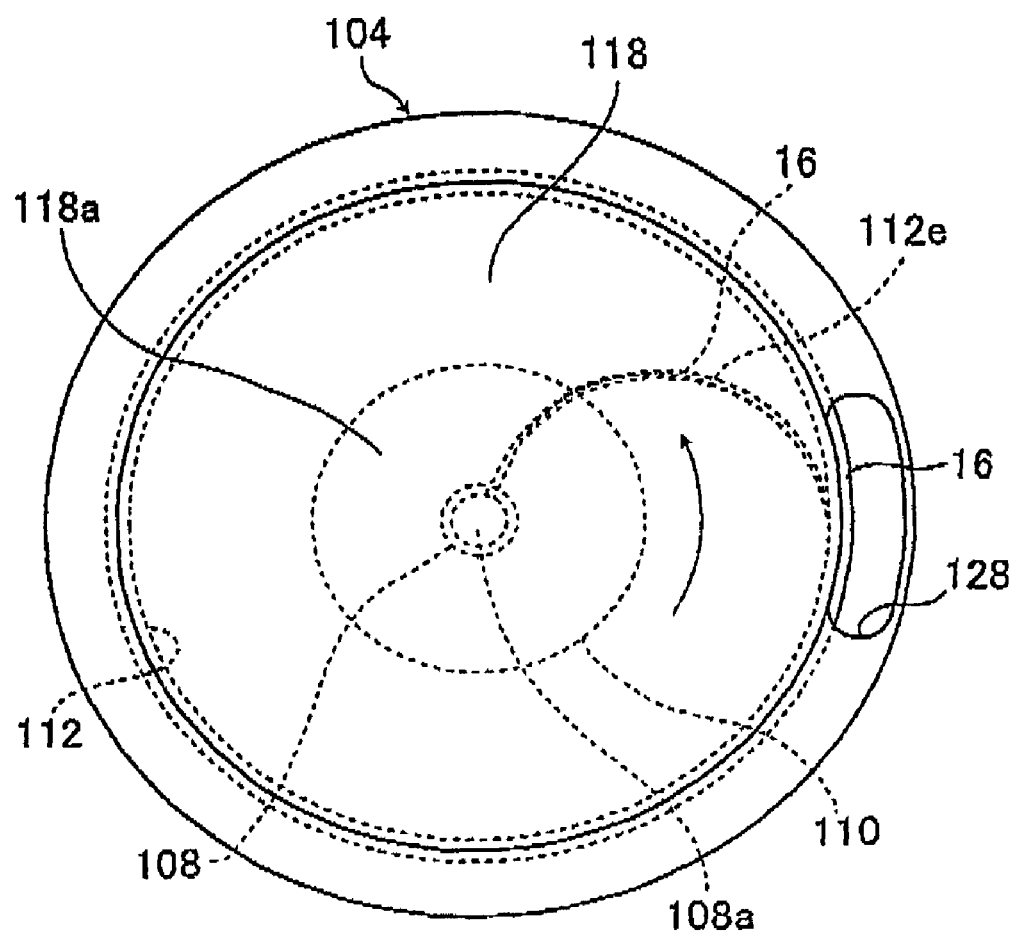
FIG. 8 is a top plan view of the extra length handling mechanism of FIG. 7.
Figure 9:
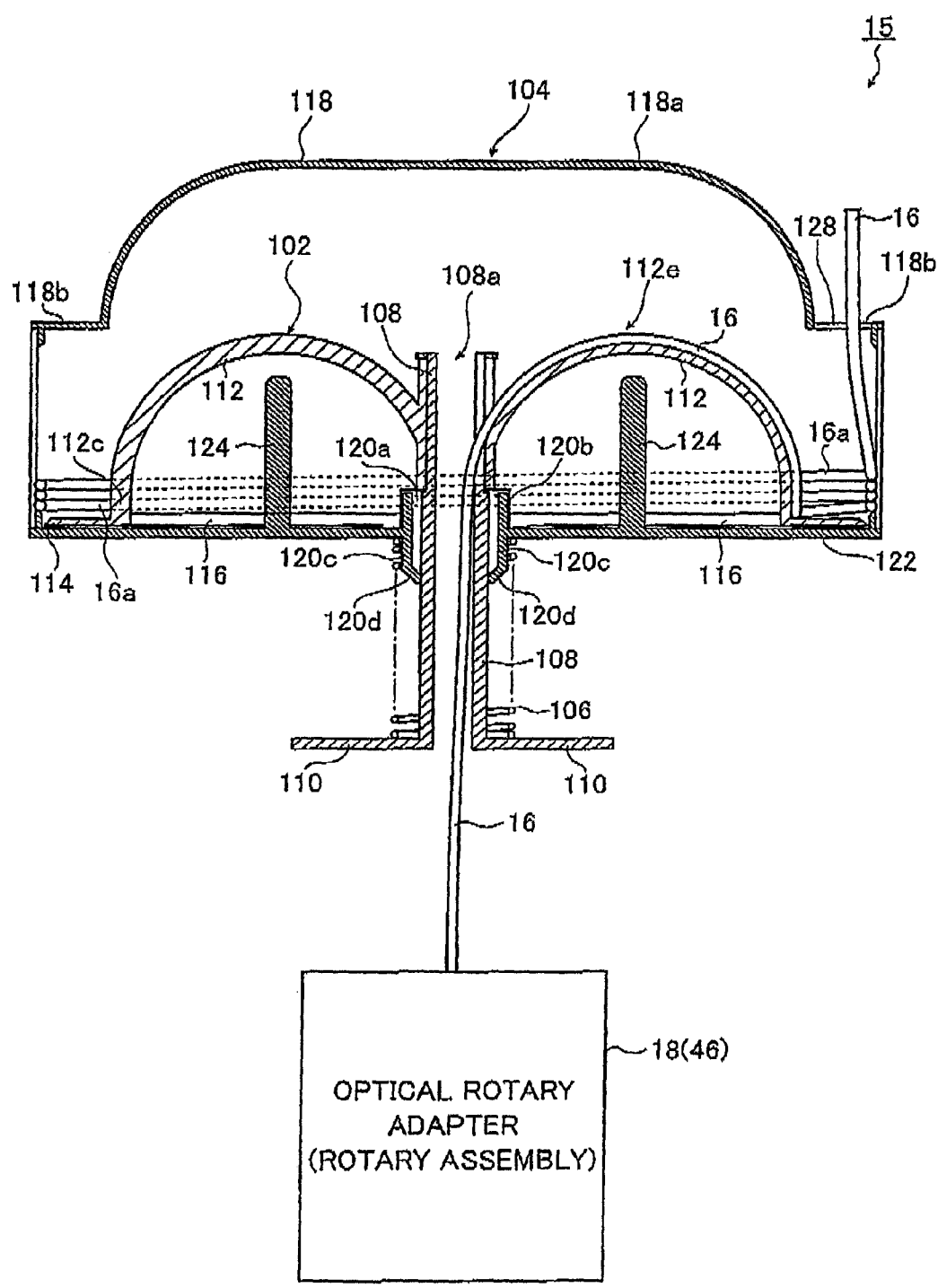
FIG. 9 is a sectional view illustrating the extra length handling mechanism of FIG. 7 in another state of use.
Figure 10:
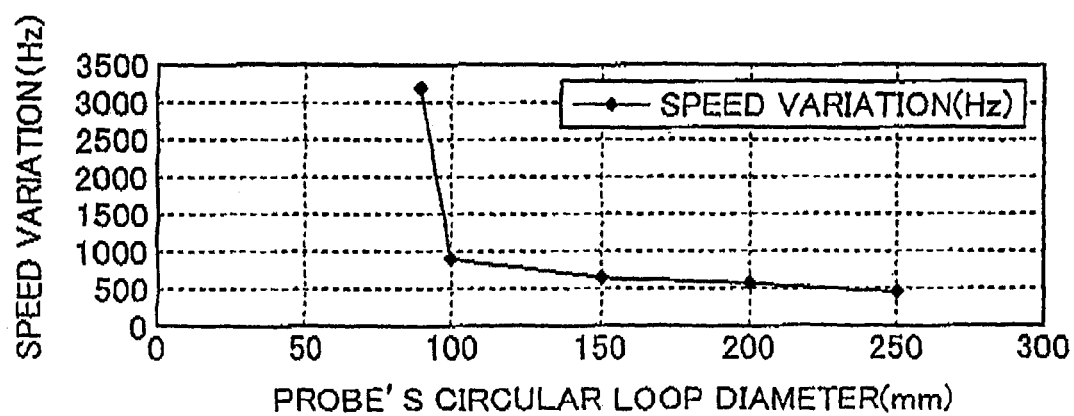
FIG. 10 is a graph illustrating an example of a correlation between the diameter of the circular loop of the optical probe of FIG. 7 and the variation in speed at the tip thereof.

FIG. 7 is a sectional view of a schematic configuration of an embodiment of the extra length handling mechanism 15 of the optical tomographic imaging system 10 of FIGS. 1 and 2, illustrating a state of the extra length handling mechanism 15 in the process of winding the optical probe 16 into the circular loop 16a in the extra length handling mechanism 15. FIG. 8 is a top plan view of the extra length handling mechanism 15. FIG. 9 is a sectional view of the extra length handling mechanism 15 in another state of use, where the optical probe 16 is in the process of being unreeled from the circular loop 16a of the extra length handling mechanism 15 to withdraw the optical probe 16. FIG. 10 is a graph illustrating an example of a correlation between the diameter of the circular loop 16a of the optical probe 16 and the variation in speed at the tip thereof.

Where one uses different lengths of the endoscope 13 for different locations to be examined such as esophagus, bronchus, lung, stomach, duodenum, and small and large intestines, the extra length handling mechanism 15 permits adjustment of the length of the optical probe 16, which is inserted into, for example, the receptacle of forceps of the endoscope 13 for use, such that one length of the optical probe applies to all the applications intended, as illustrated in FIG. 1. Thus, the extra length handling mechanism 15 is provided to wind an extra length of the optical probe 16 on the side thereof closer to its end leading to the optical rotary adapter 18 (rotary assembly 46) into the circular loop 16a having at least a given minimum diameter and hold it so wound in order to adjust the length of the optical probe 16 to an appropriate length corresponding to a length of the endoscope 13 according to the various locations to be examined, thus setting the length of the optical probe 16 from the circular loop 16a to the tip to an appropriate length.

As illustrated in FIGS. 7 to 9, the extra length handling mechanism 15 comprises a restricting guide 102 for winding the optical probe 16 into the circular loop 16a having at least a given minimum diameter, a housing 104 for accommodating the circular loop 16a of the optical probe 16 together with the restricting guide 102, and a biasing spring 106 provided between the restricting guide 102 and the housing 104.

The restricting guide 102 comprises a central circular tubing section 108 having a central through-hole 108a with a small bore for passing the optical probe 16 of which the end closer to the optical rotary adapter 18 is connected with the optical rotary adapter 18 (mounting cylinder 46a of the rotary assembly 46), a discal spring stop 110 provided around the end of the central circular tubing section 108 so as to be perpendicular to that end, a sectionally semicircular toric shell section 112 that is concentrically provided around the central circular tubing section 108 and onto which the optical probe 16 is wound, a brim section 114 provided perpendicular to the central circular tubing section 108 at the periphery of an outer base rim 112a of the toric shell section 112 on the outside, and ribs 116 provided at the bottom of the periphery of the toric shell section 112 on the inside each extending radially to connect the outer base rim 112a to an inner base rim 112b.

The central circular tubing section 108 has a shape such that part of its circumference close to the top is cut out to permit winding the inserted optical probe 16 from the inner base rim 112b immediately up onto the upper toric peripheral surface of the toric shell section 112 along a smooth arc in the direction of rotation as illustrated in FIG. 8.

As illustrated in FIG. 8, the upper toric periphery of the toric shell section 112 preferably has a semicircular groove 112e formed in the sectionally semicircular upper peripheral surface of the toric shell section 112 on the right-hand side as seen in FIG. 7 for receiving the optical probe 16 therein to permit winding the optical probe 16 onto the upper toric peripheral surface of the toric shell section 112 forming a smooth arc in the direction of rotation. The groove 112e is provided to restrict the location along which the optical probe 16 is allowed to pass. The groove 112e is formed as a curve as illustrated in FIG. 8 while FIG. 7 shows the curved groove in cross section as seen from another direction.

Since the optical probe 16 is thus fitted in the groove 112e formed in the sectionally semicircular upper periphery of the right-hand side of the toric shell section 112 as illustrated in FIG. 7 in such a manner as to be wound to a predetermined location on the toric upper periphery of the toric shell section 112, the optical probe 16 can be wound to a predetermined location on the upper toric periphery of the toric shell section 112 without a chance of the optical probe 16 being easily displaced.

The toric shell section 112 has the shape of a sectionally semicircular dome forming a continuous circle as seen from above such that the semicircular cross sections of the toric shell section 112 on both sides are symmetrical. Because of the semicircular groove 112e formed in the sectionally semicircular upper periphery of the right-hand side of the toric shell section 112 as seen in FIG. 7, the thickness of the semicircular cross section of the right-hand side of the toric shell section 112 is thinner than that of the left-hand side. Thus, the sectionally semicircular configuration of the right-hand side of the toric shell section 112 is shaped such that when the optical probe 16 is fitted in the semicircular groove 112e, the envelope of the optical probe 16 provides a symmetrical profile with respect to the semicircular cross section of the left-hand side of the toric shell section 112.

Accordingly, the toric shell section 112 is formed with the inner base rim 112b on the inside such that the arc formed by the sectionally semicircular upper periphery leads to the interior of the central circular tubing section 108 whereas the outer base rim 112a has a cylindrical section 112c extending in a straight line from the arc forming the sectionally semicircular upper periphery such that the optical probe 16 can be readily wound around the cylindrical section 112c. The cylindrical section 112c of the outer base rim 112a of the toric shell section 112 preferably has at least a diameter adequate for the circular loop 16a of the optical probe 16. More specifically, the cylindrical section 112c of the toric shell section 112 preferably has at least a minimum diameter, 100 mm, for example, such that the circular loop 16a of the optical probe 16 does not affect the rotational variation of the optical fiber FB1 inside the probe sheath 70 of the optical probe 16. Thus, the circular loop 16a preferably has at least a minimum diameter, 100 mm, for example, that does not affect the rotational variation.

The diameter of the circular loop 16a of the optical probe 16 is set according to the invention to at least a minimum diameter of, for example, 100 mm, that does not affect the rotational variation because of the findings by the inventors of the present invention that when, as illustrated in FIG. 10, the diameter of the circular loop 16a of the optical probe 16 is great, the optical fiber FB1 readily rotates inside the probe sheath 70 while as the diameter decreases, the resistance gradually increases to cause a rotational variation due to the resistance, in particular a variation in rotational speed at the tip where the optical lens 78 of the measuring unit is located; when the diameter is reduced to less than a given diameter, the resistance displays a sharp increase to cause variation in rotational speed due to the resistance at the tip. Because the rotational variation of the optical fiber FB1 inside the probe sheath 70 causes variation in rotational speed of the optical lens 78 of the measuring unit in the probe sheath 70, a great variation in rotational speed causes a great variation in rotational speed of the optical lens 78, which in turn causes variation in speed at which tomographic imaging of the object under measurement is achieved, making it impossible to acquire an image that can be appropriately used for diagnosis of a location.

Since the study by the inventors of the present invention has shown that the variation in rotational speed steeply increases when, as illustrated in FIG. 10, the circular loop 16a of the optical probe 16 decreases to less than 100 mm in the case of the optical probe used for the optical tomographic imaging system 10 inserted into the receptacle of forceps of the endoscope 13 introduced into a location to be examined such as esophagus, bronchus, lung, stomach, duodenum, and small and large intestines, to acquire optical tomographic images, the circular loop 16a of the optical probe 16 preferably has a diameter of at least 100 mm.

Since the variation in rotational speed at the tip of the optical fiber FB1 is transmitted to the rotary drive source as variation in rotational speed, the variation in rotational speed illustrated in FIG. 10 can be measured using a rotary encoder attached to the motor 36 by turning the motor 36 of the optical rotary adapter 18, which serves as a rotary drive unit, to rotate the optical fiber FB1 via the rotary assembly 46, with the circular loop 16a of the optical probe 16 having a given diameter. This is because the spring 74 in the optical probe 16 has a high torsional rigidity such that the rotational speed of the motor 36 and the rotational speed of the optical fiber FB1 at the tip thereof can be considered to be equal. For a still higher accuracy, however, the rotational speed of the optical fiber FB1 at the tip thereof was obtained by measuring the light emitted from the tip thereof using a photodetector in addition to the measuring using the rotary encoder attached to the motor 36. The measuring was conducted with the diameter of the circular loop 16a of the optical probe 16 set to 250 mm, 200 mm, 150 mm, 100 mm and 90 mm.

From FIG. 10, which is a graph illustrating an example of correlation between the diameter of the circular loop 16a of the optical probe 16 and variation in speed at the tip thereof, it appears that a diameter not less than a given diameter does not affect the rotational variation of the optical fiber FB1 in the probe sheath 70 and that the given diameter is 100 mm in the case of the optical probe 16 used for the optical tomographic imaging system 10 of the invention.

While the optical probe 16 is located along the groove 112e extending in a curve from the inner base rim 112b leading to the outer base rim 112a of the toric shell section 112, it is preferable also in this case that the loop formed by the optical probe 16 has at least a minimum diameter three-dimensionally.

Thus, when the optical probe 16 is wound to form the circular loop 16a, the circular loop 16a of the optical probe 16 cannot have a diameter less than the above minimum diameter. Therefore, the rotational variation of the optical fiber FB1 inside the probe sheath 70 of the optical probe 16 is not affected in any manner nor can the optical fiber FB1 of the optical probe 16 be accidentally damaged or broken.

There is formed at the inner base rim 112b of the toric shell section 112 an annular recess 112d into which an upper circular tubing section 120b of a central circular tubing section 120 of the housing 104 is inserted.

The housing 104 comprises a lid section 118 in the form comparable to a hat including a cap section 118a in the form of a pan and an annular brim section 118b covering the top of the toric shell section 112 of the restricting guide 102, the central circular tubing section 120 having a central through-hole 120a for inserting the central circular tubing section 108 of the restricting guide 102, a discal member 122 formed with the central circular tubing section 120 and providing a bottom plane, stoppers 124 erected along a given circumference on the discal member 122, a peripheral portion of the annular brim section 118b of the lid section 118, and a peripheral plane 126 provided between the outer edge of the annular brim section 118b of the lid section 118 and the outer edge of the discal member 122.

The cap section 118a of the lid section 118 has the shape comparable to a pan having a flat area about the center thereof and a sectionally quadrantal periphery closely covering the toric shell section 112 of the restricting guide 102 and the optical probe 16 wound onto the upper periphery thereof. The annular brim section 118b of the lid section 118 is formed with an opening 128 for passing the optical probe 16 to unreel the optical probe 16 wound onto the toric shell section 112 of the restricting guide 102 and also to wind the optical probe 16 onto the toric shell section 112.

The central circular tubing section 120 comprises the upper circular tubing section 120b projecting upwardly from the discal member 122 and a lower circular tubing section 120c projecting downwardly from the discal member 122; the lower circular tubing section 120c has an inwardly bent end 120d. Thus, as the bent end 120d is allowed to slide over the periphery of the central circular tubing section 108 of the restricting guide 102, the central circular tubing section 108 moves relative to the central circular tubing section 120 such that the restricting guide 102 and the housing 104 can be moved relative to each other.

To the periphery of the lower circular tubing section 120c of the central circular tubing section 120 and the periphery of the central circular tubing section 108 of the restricting guide 102 movably inserted in the central through-hole 120a of the central circular tubing section 120 is attached the biasing spring 106 supported between the bottom side of the discal member 122 of the housing 104 and a discal spring stop 110 formed on the lower end of the central circular tubing section 108 of the restricting guide 102.

In the state of the extra length handling mechanism 15 illustrated in FIG. 7, the spring stop 110 of the restricting guide 102 is urged toward the discal member 122 of the housing 104, and the biasing spring 106 is fully compressed to allow the restricting guide 102 to retract deepest into the housing 104 such that the toric shell section 112 of the restricting guide 102 approaches the lid section 118 of the housing 104 until a small space is left. In this state, the restricting guide 102 and the housing 104 are locked by a lock mechanism, not shown, to prevent their relative motion.

In the state of the extra length handling mechanism 15 illustrated in FIG. 7, the stoppers 124 erected on the discal member 122 of the housing 104 are short of reaching in between the ribs 116 provided to extend radially and at the bottom of the toric shell section 112 of the restricting guide 102 on the inside, allowing a gap between the tips of the stoppers 124 and the lower edges of the ribs 116.

Thus, in the extra length handling mechanism 15 illustrated in FIG. 7 where the restricting guide 102 and the housing 104 are locked to prevent their relative vertical motion, a bush 130 is located between the inner periphery of the upper circular tubing section 120b of the central circular tubing section 120 of the housing 104 and the outer periphery of the central circular tubing section 108 of the restricting guide 102 to allow the central circular tubing section 108 to relatively rotate inside the central circular tubing section 120 to permit relative rotation of the restricting guide 102 and the housing 104.

Thus, in the extra length handling mechanism 15 in the state as illustrated in FIG. 7, the relative rotation of the restricting guide 102 and the housing 104, which may be achieved, for example, by rotating the restricting guide 102 using the spring stop 110 while holding the housing 104 stationary, permits introducing the optical probe 16 through the opening 128 of the annular brim section 118b of the lid section 118 of the housing 104 to wind it onto the toric shell section 112 of the restricting guide 102 and form the circular loop 16a.

Thus, the optical probe 16 can be wound into the circular loop 16a having at least a minimum diameter that does not affect the rotational variation of the optical fiber FB1 in the probe sheath 70 of the optical probe 16.

On the other hand, the extra length handling mechanism 15 illustrated in FIG. 9 is in a state where the vertical lock described above is unlocked to allow the biasing spring 106 to urge the spring stop 110 of the restricting guide 102 away from the discal member 122 of the housing 104 until the top end of the upper circular tubing section 120b of the central circular tubing section 120 of the housing 104 touches the recess 112d of the toric shell section 112 of the restricting guide 102, with the biasing spring 106 fully stretched, thus locating the toric shell section 112 of the restricting guide 102 farthest from the lid section 118 of the housing 104.

In the state of the extra length handling mechanism 15 illustrated in FIG. 9, the stoppers 124 erected on the discal member 122 of the housing 104 are located between the ribs 116 that are provided to extend radially at the bottom of the toric shell section 112 of the restricting guide 102 on the inside and are thus engaged with the ribs 116 to prevent relative rotation of the restricting guide 102 and the housing 104.

In the extra length handling mechanism 15 in the state as illustrated in FIG. 9, since there is a gap greater than the diameter of the optical probe 16 between the top of the toric shell section 112 of the restricting guide 102 (top of the dome) and the annular brim section 118b of the lid section 118 of the housing 104 having the opening 128 formed therein for passing the probe 16 therethrough, the optical probe 16 wound onto the toric shell section 112 into the circular loop 16a is readily unreeled from the toric shell section 112 and withdrawn through the opening 128 keeping at least the minimum diameter of the loop three-dimensionally. In this case, the circular loop 16a of the optical probe 16 increases its diameter because of the elasticity and rigidity of the optical probe 16 from the state where the optical probe 16 is wound around the cylindrical section 112c of the toric shell section 112 of the restricting guide 102 until the optical probe 16 touches the peripheral plane 126 of the housing 104. That is, the optical probe 16 urges itself onto the inner periphery of the peripheral plane 126 because of the elasticity of the spring 74 inside the optical probe 16. When rounded into a circle, the optical probe 16 keeps its diameter by itself in the shape of a circle having a diameter of at least 100 mm when left free from external force because of the rigidity, etc., of the spring 74 provided inside the optical probe 16, the probe sheath 70, and the like.

Since, as described above, the extra length handling mechanism 15 of the invention is capable of winding an extra length of the optical probe 16 into a circular loop having at least a minimum diameter by winding it around the restricting guide 102, the length of the optical probe 16 used for examination can be adjusted to a proper length depending upon the location to be examined by using a single optical probe, whether the location to be examined, such as esophagus, bronchus, lung, stomach, duodenum, and small and large intestines, might otherwise require various lengths of the endoscope to be used, i.e., various lengths of the optical probe 16 to be used.

The extra length handling mechanism 15 used for the invention and the optical tomographic imaging system 10 of the invention are configured basically as described above.

Next, the operation of the optical tomographic imaging system 10 of the invention will be described.

Prior to the image taking process, in the optical rotary adapter 18, the rotary assembly 46 is removed from the fixed sleeve 38, and the optical probe 16 is removed from the rotary assembly 46. It is assumed here that the optical probe 16 has been washed.

In this state, the optical probe 16 is passed through the central through-hole 108a of the central circular tubing section 108 of the restricting guide 102 in the extra length handling mechanism 15 in the state as illustrated in FIG. 7 to be fitted in the groove 112e of the toric shell section 112, whereupon the restricting guide 102 is rotated relative to the housing 104 to wind an extra length of the optical probe 16 into the circular loop 16a around the cylindrical section 112c such that the optical probe 16 is sufficiently reeled in to reduce its length to, say a minimum, for example. Then, the rotary assembly 46 with the optical probe 16 attached thereto is rotatably mounted to the fixed sleeve 38 in the optical rotary adapter 18.

Subsequently, the extra length handling mechanism 15 is placed in the state as illustrated in FIG. 9, and the optical probe 16 is unreeled by a proper length depending upon a length to the object under measurement that varies with the location to be examined, to prepare for producing optical tomographic images of the object under measurement S at the location to be examined with the optical tomographic imaging system 10. Thus, the length of the optical probe 16 can be adjusted to a proper length depending upon a length up to the object under measurement S that varies with the location to be examined.

Where the length up to the object under measurement S that varies with the location to be examined is known, the length of the optical probe 16 may have been adjusted to a proper length to suit a length up to the object under measurement S that varies with the location to be examined, prior to attaching the rotary assembly 46 to the fixed sleeve 38 in the optical rotary adapter 18. Further, instead of disassembling the optical rotary adapter 18, the optical probe 16 may be detached from or attached to the connecting unit 46c of the rotary assembly 46 of the optical rotary adapter 18.

Subsequently, optical tomographic imaging of the object under measurement S at the location to be examined is performed by the optical tomographic imaging system 10.

Description will be first made as to how the interference light and the interference signal are acquired upon measuring the object under measurement S.

First, the mirror moving mechanism 88 is activated to move the base 86 in the direction indicated by the arrow A to adjust and set the optical path length such that the object under measurement S is positioned within a measurable range.

Thereafter, the light source unit 12 emits the laser beam La. The emitted laser beam La is split by the splitter/combiner 14 into the measuring light L1 and the reference light L2. The measuring light L1 is guided through the optical fiber FB2, the optical rotary adapter 18, and the optical probe 16 (optical fiber FB1) to radiate the object under measurement S.

The optical rotary adapter 18 meanwhile is rotating the optical fiber FB1 and the optical lens 78 in the optical probe 16. More specifically, in the optical rotary adapter 18, the motor 36 is activated to turn the rotary shaft 36a and the gear 54 mounted at the end thereof, causing the gear 52 in mesh with the gear 54 to turn by the intermediate of the rotary cylinder 46b of the rotary assembly 46, the rotation of the gear 52 turns the mounting cylinder 46a rotatably carried by the fixed sleeve 38 via the bearings 44. This in turn rotates the optical fiber FB1 held substantially at the center of the mounting cylinder 46a by the holder 48a, etc. Since the optical fiber FB1 held inside the rotary assembly 46 (rotary cylinder 46b) is connected to the optical fiber FB1 encased in the optical probe 16 at the connecting unit 46c of the rotary cylinder 46b or extends into the optical probe 16 via the connecting unit 46c of the rotary cylinder 46b of the rotary cylinder 46b, the rotation of the optical fiber FB1 encased in the rotary cylinder 46b turns the optical fiber FB1 inside the optical probe 16 and the optical lens 78 that is attached at the tip thereof.

Meanwhile, the measuring light L1 transmitted by the optical fiber FB2 held by the holder 40a of the fixed sleeve 38 and emitted from the inclined end face of the optical fiber FB2 enters the collimating lens 42 held by the holder 40b of the fixed sleeve 38 and then, after collimation, the collimating lens 50 held by the holder 48b attached to the rotating mounting cylinder 46a. The measuring light L1 is then focused and allowed to enter the inclined end face of the optical fiber FB1 held by the holder 48a mounted to the holder 48b. The measuring light L1 is then transmitted into the optical fiber FB1 inside the optical probe 16 to enter the optical lens 78 and directed by the optical lens 78 to pass through the probe sheath 70, irradiating the object under measurement S.

Since the optical rotary adapter 18 is meanwhile rotating the optical fiber FB1 and the optical lens 78 in the optical probe 16, the object under measurement S such as a bodily cavity is irradiated with the measuring light L1 throughout the circumference thereof by means of the rotating optical lens 78. Meanwhile, the optical rotary adapter 18 detects information on the measuring position of the object under measurement S using a rotary encoder (not shown).

Subsequently, the light reflected at individual depth positions of the object under measurement S enters the optical probe 16 as the returning light L3. Since the optical rotary adapter 18 is still rotating the optical fiber FB1 and the optical lens 78 inside the optical probe 16, the returning light L3 from the object under measurement S for the whole circumference of the object under measurement S enters the rotating optical lens 78. This returning light L3 is delivered to the splitter/combiner 14 through the optical probe 16 (optical fiber FB1), the optical rotary adapter 18, and the optical fiber FB2.

The returning light L3 from the object under measurement S is transmitted through the outer probe sheath 70 of the optical probe 16 to enter the rotating optical lens 78, then transmitted therefrom to the optical fiber FB1 in the optical probe 16, and enters the optical fiber FB1 held by the holder 48a inside the rotary assembly 46 of the optical rotary adapter 18. In the optical rotary adapter 18, the returning light L3 emitted from the inclined end face of the rotating optical fiber FB1 enters the collimating lens 50 held by the holder 48b inside the rotating rotary assembly 46 and, after collimation, the collimating lens 42 held by the holder 40b of the stationary fixed sleeve 38. The returning light L3 is then focused to enter the inclined end face of the optical fiber FB2 held by the holder 40a of the fixed sleeve 38 and delivered through the optical fiber FB2 to the splitter/combiner 14.

In the optical rotary adapter 18, since the respective optical axes of the rotary optical fiber FB1 and the stationary optical fiber FB2 are offset from the center of rotation, i.e. the center of rotation of the rotary assembly 46 (mounting cylinder 46a), each by a given amount, the attenuation of the returning light L3 can be lessened to reduce white noise and improve the signal-to-noise ratio of the returning light L3.

Meanwhile, the reference light L2 is delivered through the optical fiber FB5 to the optical path length adjuster 26. The reference light L2 having its optical path length adjusted by the optical path length adjuster 26 is guided through the optical fiber FB5 back to the splitter/combiner 14.

The splitter/combiner 14 combines the returning light L3 from the object under measurement S with the reference light L2 having its optical path length adjusted by the optical path length adjuster 26, generating the interference light L4 from the returning light L3 and the reference light L2. The interference light is detected as interference signal by the interference light detector 20.

Then, the interference signal detected by the interference light detector 20 is sent to the processor 22.

In the processor 22, the interference signal acquirer 90 acquires the interference signal it receives as well as information on the measuring position detected by the optical rotary adapter 18 to correlate the interference signal with the information on the measuring position.

Then, the analog-to-digital converter 92 converts the interference signal acquired by the interference signal acquirer 90 and correlated with the information on the measuring position from analog signal to digital signal. The interference signal now correlated with the information on the measuring position and converted to digital signal is sent from the analog-to-digital converter 92 to the contact area detector 94 and the tomographic information generator 96.

The contact area detector 94 detects the contact area of the probe sheath 70 and the object under measurement S, whereupon the information on the detected contact area of the probe sheath 70 and the object under measurement S is sent to the tomographic information generator 96.

From the contact area information sent from the contact area detector 94, the tomographic information generator 96 processes the information on the relationship between frequency component and intensity obtained by applying FFT to the interference signal converted into digital signal by the analog-to-digital converter 92 only where the interference signal is correlated with the information on the position judged to be a contact area to acquire a depthwise tomographic information for the contact area. The tomographic image acquired by the tomographic information generator 96 is sent to the image corrector 98.

The image corrector 98 performs logarithmic conversion and radial conversion on the tomographic image generated by the tomographic information generator 96 to make it a circular tomographic image the center of which registers with the center of rotation of the optical lens 78, as well as sharpening processing and smoothing processing and the like to correct the image quality.

The tomographic image with the image quality corrected by the image corrector 98 is sent to the display 24.

The display 24 shows the tomographic image sent from the image corrector 98 as an image after image quality correction.

After image taking is completed, the optical probe 16 is unreeled entirely from the extra length handling mechanism 15 in the state as illustrated in FIG. 9 and withdrawn therefrom whereas the rotary assembly 46 is removed together with the optical probe 16 from the fixed sleeve 38 of the optical rotary adapter 18 to wash the optical probe 16.

Thereafter, the optical probe 16 is wound by a sufficient length into the circular loop 16a in the extra length handling mechanism 15 as described above to stand by for the next round of image taking.

While the optical tomographic imaging systems 10 described above uses SS-OCT (swept source-OCT) measuring method to detect the contact area with the object under measurement and thereby acquire a tomographic image of the object under measurement, the invention is not limited in this way and may use any other OCT measuring method. The other OCT measuring methods that may be used here include, for example, an SD-OCT (spectral domain-OCT) measuring method and a TD-OCT (time domain-OCT) measuring method.

While the optical tomographic imaging system of the invention has been described in detail by reference to various embodiments thereof, the present invention is not limited in any manner to these embodiments, and various improvements and modifications may be made without departing from the spirit of the invention.

For example, while the fixed sleeve and the rotary assembly of the optical rotary adapter are provided each in a one-piece configuration in the above embodiments, any other configuration may be used, provided that the rotary optical transmission system composed of the rotary optical fiber and the rotary collimating lens can be integrally provided and the stationary optical transmission system composed of the stationary optical fiber and the stationary collimating lens can be integrally provided, that the rotary optical transmission system can be rotatably supported with respect to the stationary optical transmission system, and that the respective optical axes of the rotary optical fiber and the stationary optical fiber are offset from the center of rotation (e.g., the center of rotation of the rotary assembly, i.e., the mounting cylinder and the rotary cylinder) by a given amount to lessen the attenuation of the returning light from the object under measurement, reduce white noise and improve the signal-to-noise ratio of the returning light. For example, the composite parts of the fixed sleeve, the mounting cylinder and the rotary cylinder of the rotary assembly, and the connecting unit, such as the discal section, the circular tubing section, and cylindrical sections may be provided as discrete component parts. Further, any configuration may be used provided that the rotary optical transmission system can be rotatably and removably supported with respect to the stationary optical transmission system.

What is claimed is:

1. An optical tomographic imaging system comprising:
a main body of system for acquiring an optical tomographic image of an object under measuring;
an optical probe having a given length and including a first optical fiber rotatably provided for guiding measuring light from said main body of system to said object under measurement and guiding returning light from said object under measurement to said main body of system, a measuring unit disposed at a tip of said first optical fiber for irradiating said object under measurement with said measuring light and acquiring returning light from said object under measurement, and a probe sheath covering the peripheries of said first optical fiber and said measuring unit so as to rotatably hold said first optical fiber and said measuring unit and having at least a region thereof formed of a transparent material transmitting said measuring light from said measuring unit and said returning light from said object under measurement;
a second optical fiber stationarily provided and connected with said main body of system for guiding said measuring light to said first optical fiber and guiding said returning light guided by said first optical fiber to said main body of system;
a rotary drive unit provided between said optical probe and said second optical fiber for rotatably connecting said measuring unit and said first optical fiber following said measuring unit in said optical probe to said second optical fiber to transmit said measuring light and said returning light;
an extra length handling mechanism for winding said optical probe into a circular loop having at least a given minimum diameter on a side closer to said rotary drive unit and holding said probe so wound; and
attaching and detaching means for attaching and detaching said optical probe at said rotary drive unit or between said rotary drive unit and said extra length handling mechanism,
wherein said main body of system acquires said optical tomographic image of said object under measurement using said guided returning light,
wherein said extra length handling mechanism winds an extra length of said optical probe according to said object under measurement to set a length extending from said extra length handling mechanism to a tip of said optical probe,
wherein said extra length handling mechanism winds said extra length of said optical probe into the circular loop through a center of the circular loop from a direction perpendicular to the circular loop and comprises a restricting guide for winding said optical probe into said circular loop having at least a given minimum diameter,
wherein said restricting guide comprises a first central circular tubing section for passing said optical probe and a sectionally semicircular toric shell section that is concentrically provided around said first central circular tubing section and around which said optical probe is wound into the circular loop,
wherein said sectionally semicircular toric shell section comprises an inner base rim provided in a direction perpendicular to said first central circular tubing section and integrated with said first central circular tubing section, an outer base rim provided in parallel to said first central circular tubing section, and a toric peripheral surface formed between said inner base rim and said outer base rim, and wherein said optical probe passes through an inside of said first central circular tubing section, extends from one end of said first central circular tubing section in the direction perpendicular to said first central circular tubing section, and is wound on a periphery of said outer base rim of said sectionally semicircular toric shell section to form the circular loop.

2. The optical tomographic imaging system according to claim 1, wherein said extra length handling mechanism comprises a storage unit for storing said optical probe wound into said circular loop having at least a given minimum.

3. The optical tomographic imaging system according to claim 1, wherein said extra length handling mechanism comprises a mechanism for winding an extra length of said optical probe into a circular loop having a diameter of 100 mm or more not affecting rotational variation of said first optical fiber in said probe sheath of said optical probe.

4. The optical tomographic imaging system according to claim 1, wherein said rotary drive unit is an optical rotary adapter or an optical rotary joint for rotatably connecting said first optical fiber of said optical probe to said second optical fiber spaced with a given distance between these optical fibers to transmit said measuring light and said returning light.

5. The optical tomographic imaging system according to claim 1, wherein said attaching and detaching means is provided in said rotary drive unit to attach and detach said first optical fiber of said optical probe to said second optical fiber.

6. The optical tomographic imaging system according to claim 1, wherein said attaching and detaching means is an optical connector coupling unit or an optical adapter connecting mechanism provided between said extra length handling mechanism and said rotary drive unit to removably attach said first optical fiber of said optical probe.

7. The optical tomographic imaging system according to claim 1, wherein said optical probe is inserted into an endoscope introduced to a location to be examined such that a tip portion where said measuring unit is positioned is placed into contact with said object under measurement at said location to be examined for measurement, said optical probe being wound into said extra length handling mechanism by a length depending upon an insertion length up to said location to be examined to which said endoscope is introduced to set a length of said first optical fiber extending beyond said extra length handling mechanism.

8. The optical tomographic imaging system according to claim 1, wherein said main body of system comprises
  a light source;
  a splitter for splitting light emitted from said light source into said measuring light and reference light;
  a combiner for combining said returning light detected by said measuring unit of said optical probe and guided through said first optical fiber, said rotary drive unit, and said second optical fiber with said reference light to produce an interference light;
  an interference light detector for detecting said interference light as an interference signal; and
  a tomographic image acquirer for acquiring said optical tomographic image from said interference signal detected by said interference light detector.

9. The optical tomographic imaging system according to claim 8, wherein said light source emits light as it sweeps a wavelength with a constant period.

10. The optical tomographic imaging system according to claim 1,
  wherein said sectionally semicircular toric shell section further comprises a semicircular groove for receiving said optical probe therein which is formed in said tonic peripheral surface along an outer peripheral surface of said toric peripheral surface so as to permit winding said optical probe onto said outer peripheral surface of said toric peripheral surface while forming a smooth arc in a direction of rotation of said restricting guide.

11. The optical tomographic imaging system according to claim 1, wherein said first central circular tubing section has a shape such that a part of said one end of said first central circular tubing section is cut out to permit winding said optical probe inserted within said first central circular tubing section from said inner base rim of said sectionally semicircular toric shell section immediately up onto said outer peripheral surface of said toric peripheral surface along a smooth arc formed in a direction of rotation of said restricting guide.

12. The optical tomographic imaging system according to claim 1, wherein said extra length handling mechanism further comprises:
  a housing for accommodating rotatably said restricting guide on which said optical probe is wound into said circular loop; and
  a biasing spring provided between said restricting guide and said housing.

13. The optical tomographic imaging system according to claim 12, wherein said restricting guide further comprises:
  a discal spring stop for receiving said biasing spring that is provided around another end of said first central circular tubing section so as to be perpendicular to said another end;
  a brim section provided perpendicular to said first central circular tubing section at an outer periphery of said outer base rim of said sectionally semicircular toric shell section; and
  ribs provided at a bottom of an inner periphery of said sectionally semicircular toric shell section, each rib extending radially to connect said outer base rim to said inner base rim.

14. The optical tomographic imaging system according to claim 13, wherein said housing comprises:
  a lid section in a form of a hat including a cap section in a form of a pan and an annular brim section extending from said cap section in a direction perpendicular to said first central circular tubing section of said restricting guide, said lid section covering a top of said sectionally semicircular toric shell section of said restricting guide;
  a second central circular tubing section having a central through-hole for inserting said first central circular tubing section of said restricting guide;
  a discal member formed with said second central circular tubing section and providing a bottom plane;
  stoppers erected along a given circumference on said discal member; and
  a peripheral plane provided between an outer edge of said annular brim section of said lid section and an outer edge of said discal member.

15. The optical tomographic imaging system according to claim 14,
  wherein said biasing spring is supported between a bottom side of said discal member of said housing and said discal spring stop formed on said another end of said first central circular tubing section of said restricting guide,
  wherein, in a state where said biasing spring is fully compressed, and said sectionally semicircular tonic shell section of said restricting guide approaches said lid section of said housing, said stoppers of said housing are away from said ribs of said restricting guide in a direction parallel to said first central circular tubing section and not engaged with said ribs to allow said first central circular tubing section of said restricting guide to relatively rotate inside said second central circular tubing section of said housing to permit relative rotation of said restricting guide and said housing, so that said optical probe is wound on said restricting guide in said circular loop, or rewound from said circular loop wound on said restricting guide, and wherein, in a state where said biasing spring is fully stretched, and said sectionally semicircular toric shell section of said restricting guide is away from said lid section of said housing, said stoppers of said housing are engaged with said ribs to prevent the relative rotation of said restricting guide and said housing.

* * * * *